(12) United States Patent
Itoh et al.

(10) Patent No.: US 7,683,218 B2
(45) Date of Patent: Mar. 23, 2010

(54) METHOD FOR PRODUCING THIOETHER COMPOUND

(75) Inventors: Takahiro Itoh, Ibaraki (JP); Toshiaki Mase, Ibaraki (JP); Atsushi Akao, Ibaraki (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 396 days.

(21) Appl. No.: 11/664,663

(22) PCT Filed: Oct. 7, 2005

(86) PCT No.: PCT/JP2005/018985

§ 371 (c)(1),
(2), (4) Date: Apr. 4, 2007

(87) PCT Pub. No.: WO2006/038741

PCT Pub. Date: Apr. 13, 2006

(65) Prior Publication Data

US 2008/0108823 A1 May 8, 2008

(30) Foreign Application Priority Data

Oct. 8, 2004 (JP) .............................. 2004-295958

(51) Int. Cl.
*C07C 319/16* (2006.01)
(52) U.S. Cl. ........................................ 568/58
(58) Field of Classification Search .................... 568/58
See application file for complete search history.

(56) References Cited

U.S. PATENT DOCUMENTS

2004/0106653 A1 6/2004 Sakurai et al.
2006/0258701 A1 11/2006 Mitsuya et al.

FOREIGN PATENT DOCUMENTS

JP 2002-47278 2/2002
WO WO 2004/081001 9/2004

OTHER PUBLICATIONS

S. W. Kaldor et al., "Viracept (Nelfinavir Mesylate, AG1343): A Potent, Orally Bioavailable Inhibitor of HIV-1 Protease", J. Med. Chem., vol. 40, pp. 3979-3985 (1997).
N. Zheng et al., "Palladium-Catalyzed Synthesis of Aryl Sulfides from Aryl Triflates", J. Org. Chem., vol. 63, pp. 9606-9607 (1998).
G. Y. Li et al., "Highly Active, Air-Stable Versatile Palladium Catalysts for the C-C, C-N, and C-S Bond Formations via Cross-Coupling Reactions of Aryl Chlorides", J. Org. Chem., vol. 66, pp. 8677-8681 (2001).
U. Schopfer et al., "A general palladium-catalysed synthesis of aromatic and heteroaromatic thioethers", Tetrahedron, vol. 57, pp. 3069-3073 (2001).
T. Migita et al., "The Palladium Catalyzed Nucleophilic Substitution of Aryl Halides by Thiolate Anions", Bull. Chem. Soc. Japan, vol. 53, pp. 1385-1389 (1980).
F. Y. Kwong et al., "A General, Efficient, and Inexpensive Catalyst System for the Coupling of Aryl Iodides adn Thiols", Organic Letters, vol. 4, No. 20, pp. 3517-3520 (2002).
S. Rajagopalan et al., "Synthesis of N-$t$-BOC-4-S-$t$-Butyl-L-Thiophenylalanine Via Palladium Catalyzed Cross-Coupling Reaction of N-$t$-BOC-4-IODO-L-Phenylalanine with $t$-Butylthiol or Sodium $t$-Butylthiolate", Synthetic Communications, vol. 26, No. 7, pp. 1431-1440 (1996).
J. E. T. Corrie et al., "Synthesis of a Cephalosporin Analogue", Journal of Chemical Society, Perkin Transaction, Chapter I, p. 1421-1425 (1977).
S. Sakakibara et al., "Use of Anhydrous Hydrogen Fluoride in Peptide Synthesis. I. Behavior of Various Protective Groups in Anhydrous Hydrogen Fluoride", Bulletin of the Chemical Society of Japan, vol. 40, pp. 2164-2167 (1967).
D. A. J. Ives, "Electrolysis in liquid ammonia solution in peptide chemistry", Canadian Journal of Chemistry, vol. 47, pp. 3697-3699 (1969).
A. Ogawa et al., "Highly Regio- and Stereocontrolled Synthesis of Vinyl Sulfides via Transition-Metal-Catalyzed Hydrothiolation of Alkynes with Thiols", J. Am. Chem. Soc., vol. 121, pp. 5108-5114 (1999).
T. Itoh et al., "A General Palladium-Catalyzed Coupling of Aryl Bromides/Triflates and Thiols", Organic Letters, vol. 6, No. 24, pp. 4587-4590 (2004).
M. Harr et al., "Palladium Catalyzed Bispyrimidine Thioether Synthesis", Synlett, vol. 10, pp. 1579-1581 (1999).

*Primary Examiner*—Taofiq A Solola
(74) *Attorney, Agent, or Firm*—Richard C. Billups; Catherine D. Fitch

(57) ABSTRACT

Disclosed is an efficient and widely-applicable method for commercially producing a thioether compound or a thiol compound which is useful as a pharmaceutical compound or a production intermediate of it. Specifically disclosed is a method for producing a thioether compound represented by the general formula [I] below or a salt thereof. This method is characterized in that a compound represented by the following general formula [III]: [III] (wherein X represents a bromine atom, a chlorine atom or a trifluoromethylsulfonyloxy group, and ring A represents an aryl group or a heteroaryl ring group) or a salt thereof is reacted with a thiol compound represented by the following general formula [II]: [II] or a salt thereof in the presence of a palladium compound such as $Pd_2(dba)_3$, a base such as i-$Pr_2$NEt and a phosphorus compound represented by the following formula [AA].

25 Claims, No Drawings

METHOD FOR PRODUCING THIOETHER COMPOUND

CROSS REFERENCE TO RELATED APPLICATIONS

This application is a U.S. national phase application based upon PCT JP2005/018985 filed in Japan on Oct. 7, 2005, which claims the benefit of Japanese Provisional Application No. JP 2004-295958 filed on Oct. 8, 2004, priority of which is claimed hereunder.

TECHNICAL FIELD

The present invention relates to an efficient and novel method for producing a thioether compound or a thiol compound useful as a pharmaceutical compound or a production intermediate of it.

BACKGROUND ART

Thioether compounds are disclosed useful as pharmaceutical compounds. For example, it is disclosed that a thioether compound having the following chemical structural formula, Viracept (AG1343) has an HIV-1 protease-inhibitory effect and is industrialized as a treating agent for AIDS (see Stephen W. Kaldor, et al., Journal of Medicinal Chemistry, Vol. 40, pp. 3979-3985 (1997)).

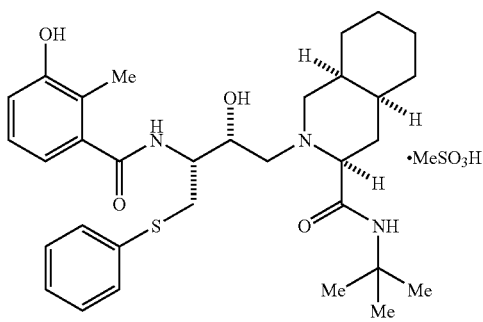

Viracept (AG1343)

WO2004/081001 discloses thioether compounds useful as a treating agent and/or a preventing agent for diabetes and also as a treating agent and/or a preventing agent for diabetes complications.

On the other hand, the following method is known for producing thioether compounds (see Nan Zheng, et al., Journal of Organic Chemistry, Vol. 63, p. 9606-9607 (1998)).

In this non-patent reference, as a weak base, $K_2CO_3$, $NaHCO_3$ and Triethylamine are used for the reaction, in which, however, the yield of the thioether compound is low, and the method is therefore unsuitable for industrial-scale production. This patent reference 2 says that the production method for thioether compounds disclosed therein is not applicable to a thiol nucleophile such as benzene thiol. In other words, it may be said that the production method could not produce diaryl sulfides.

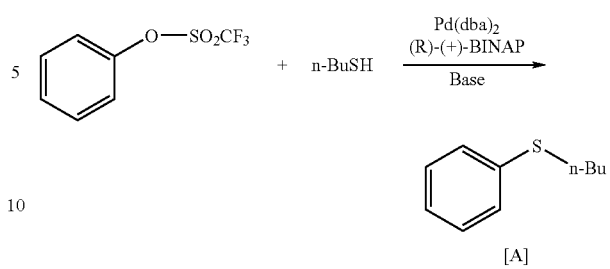

| Base | Yield of Compound [A] |
|---|---|
| $K_2CO_3$ | 57% |
| $NaHCO_3$ | 27% |
| triethylamine | 65% |

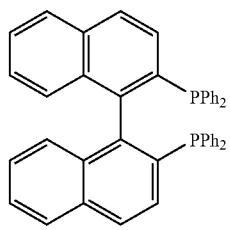

Further, it is known to produce a thioether compound by the use of a palladium compound such as POPD1, POPD2 or POPD, and a strong base such as KOtBu (see George Y. Li, et al., Journal of Organic Chemistry, Vol. 66, pp. 8677-8681 (2001)).

The palladium compound is poor in universal applicability and is expensive, and therefore the production method for thioether compounds is unsuitable for industrial-scale production.

POPD1

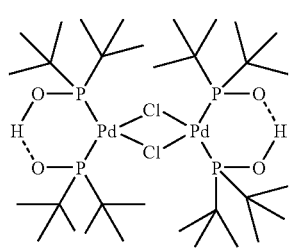

POPD2

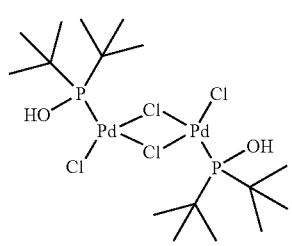

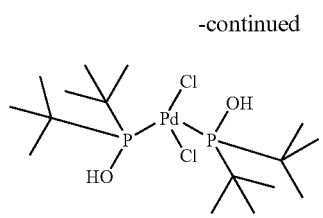

Also known is a method for producing thioether compounds, using $Pd_2(dba)_3$ and DPEphos and, as a base, $CsCO_3$ (see Ulrich Schopfer, et al., Tetrahedron, Vol. 57, pp. 3069-3073 (2001)). According to the production method, the yield of the intended thioether compound is low, and the method is unsuitable for industrial use.

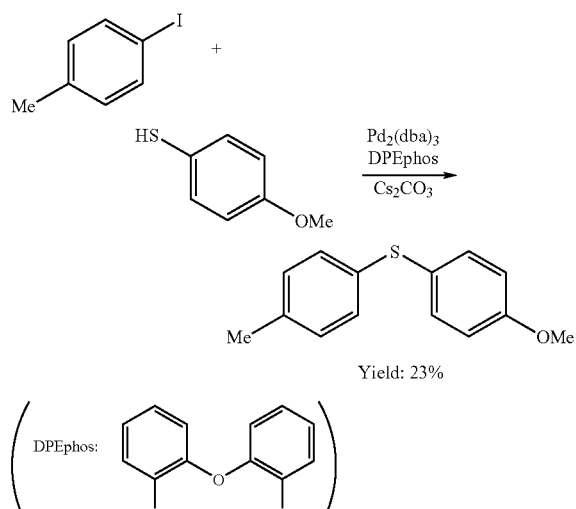

Also known is a method for producing thioether compounds, using $Pd(PPh_3)_4$ and t-BuONa (strong base) (see Toshihiko Migita, et al., Bulletin of the Chemical Society of Japan, Vo. 53, pp. 1385-1389 (1980)).

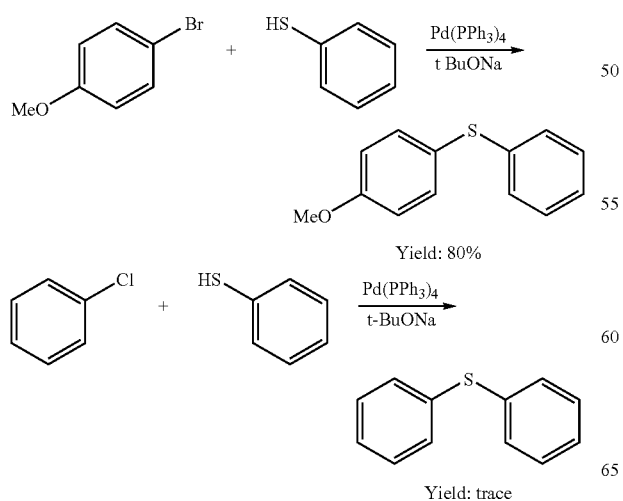

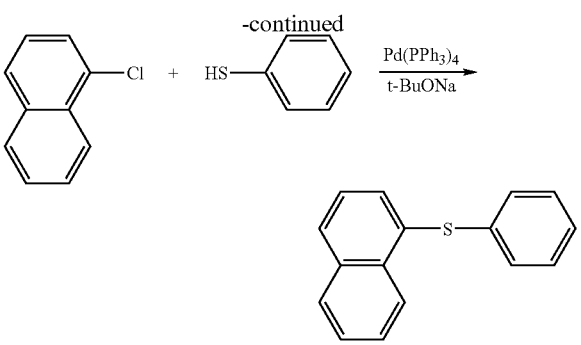

Also known is a method for producing thioether compounds, using CuI and $K_2CO_3$ (Fuk Yee Kwong, et al., Organic Letters, Vol. 4, pp. 3517-3520 (2002)).

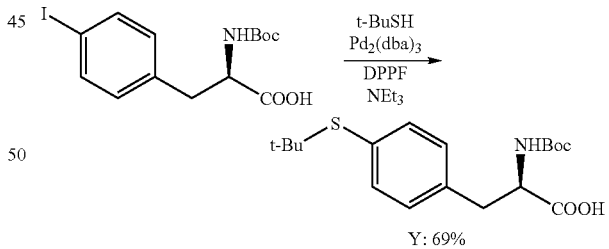

Also disclosed is a case of producing alkylthioether compounds, starting from an iodine compound (Shyamala Rajagopalan, et al., Synthetic Communications, Vol. 26, No. 7, pp. 1431-1440 (1996)). As starting from an iodine compound, the production method is poor in universal applicability.

Also disclosed is an example of the following reaction case (see JP-A 2002-47278). The yield in the reaction case is too low for industrial-scale production, and the method is unsuitable for industrial use.

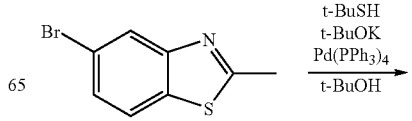

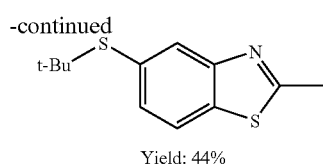

Yield: 44%

For removing a benzyl group or a phenyl group bonding to a thiol group, the following methods are known.

(a) Treatment with metal sodium in liquid ammonia (see J. E. T Corrie, et al., Journal of Chemical Society, Perkin Transaction, Chap. I, p. 1421 (1977)).

(b) Treatment with hydrogen fluoride in anisole (see S. Sakakibara, et al., Bulletin of Chemical Society of Japan, Vol. 40, p. 4126 (1967)).

(c) Electrolysis (see D. A. J. Ives, Canadian Journal of Chemistry, Vol. 47, 3697 (1969)).

The above methods may use reagents dangerous and unsuitable for industrial-scale production that requires use of a large amount of chemicals, and may require specific production equipment such as electrolytic cells, and therefore these are unfavorable for industrial application in some points.

The present invention is to develop a production method capable of efficiently producing a thioether compound or a thiol compound useful as a pharmaceutical compound or a production intermediate of it, as disclosed in Stephen W. Kaldor, et al., Journal of Medicinal Chemistry, Vol. 40, pp. 3979-3985 (1997) and WO2004/081001.

DISCLOSURE OF THE INVENTION

We, the present inventors have assiduously studied a method for producing thioether compounds and, as a result, have found a novel method for producing a thioether compound, in which a phosphorus compound, a palladium compound and a weak base are used, and a bromide, a chloride or a sulfonate compound that are readily available as starting materials are used to produce a thioether compound at high yield under mild basic condition, and on the basis of this finding, we have completed the present invention.

Further, we have also found out an efficient method for introducing a thiol group into an aryl ring or a heteroaryl ring, taking advantage of the novel production method for a thioether compound, and have completed the invention.

Specifically, the method for producing a thioether compound and the production method for a thiol compound of the invention have the following advantages for industrial-scale production of the compounds.

(a) The method for producing a thioether compound of the invention can be carried out under a mild basic condition, and is therefore applicable to a compound unstable under a strong basic condition.

(b) In the method for producing a thioether compound of the invention, a bromide, a chloride or a sulfonate compound that are less reactive than an iodine compound may be used as starting materials for producing thioether compounds.

(c) In the method for producing a thioether compound of the invention, a bromide, a chloride or a sulfonate compound may be used as starting materials, and therefore the application latitude of the method is broader than that of any known methods using an iodine compound, and the starting materials for the method are readily available.

(d) According to the method for producing a thioether compound of the invention, a thiol compound substituted with a removable group may be reacted with an aryl or heteroaryl compound having a chloride group, a bromide group or a substituted sulfonyl group to thereby efficiently produce a thioether compound, and then the removable group may be removed to thereby efficiently introduce a thiol group into the aryl ring or the heteroaryl ring.

(e) In case where the removable group is a substituted or unsubstituted benzyl group, or a substituted or unsubstituted phenethyl group, it may be removed in any ordinary equipment under a simpler and milder condition than in any other conventional method.

Specifically, the invention relates to the following (1) to (21):

(1) A method for producing a thioether compound or its salt of a general formula:

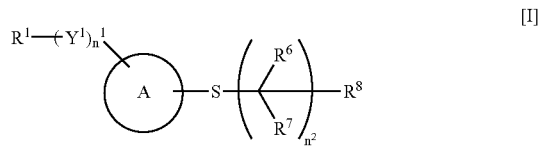

[I]

wherein $R^1$, $Y^1$, $R^6$, $R^7$, $R^8$, $n^1$, $n^2$ and a group of a general formula:

have the same meanings as mentioned below, which comprises reacting an aryl or heteroaryl compound or its salt of a general formula [III]

[III]

wherein $R^1$ represents a hydrogen atom, a halogen atom, a cyano group, an alkyl group having from 1 to 10 carbon atoms, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, or an alkanoyl group having from 1 to 10 carbon atoms;

$Y^1$ represents an alkylene group having from 1 to 6 carbon atoms of which the carbon chain may have a group selected from a sulfur atom, a sulfinyl group, a sulfonyl group, an oxygen atom, a carbonyl group, an oxycarbonyl group, a carbonyloxy group and a group of a general formula:

wherein $R^2$ represents a hydrogen atom, an alkyl group having from 1 to 6 carbon atoms, a benzyl group, a phenyl group, a naphthyl group or a pyridyl group;

X represents a bromine atom, a chlorine atom, a trifluoromethanesulfonyloxy group, a methylsulfonyloxy group, a benzenesulfonyloxy group, a toluenesulfonyloxy group or a nitrobenzenesulfonyloxy group;

$n^1$ indicates 0 or 1;

the group of a general formula:

means an aryl ring group or a heteroaryl ring group;

provided that when X is a chlorine atom, then the group of a general formula:

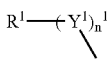

is an electron-withdrawing group, wherein $R^1$, $n^1$ and $Y^1$ have the same meanings as above;

with a thiol compound or its salt of a general formula [II]:

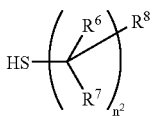

wherein $R^6$ and $R^7$ may be the same or different, each representing a hydrogen atom, an alkyl group having from 1 to 6 carbon atoms, an amino group, or a phenyl group;

$n^2$ indicates from 0 to 6;

$R^8$ represents a hydrogen atom, a halogen atom, a cyano group, an amino group, an alkyl group having from 1 to 10 carbon atoms, a trimethylsilyl group, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, an alkanoyl group having from 1 to 10 carbon atoms, or a group of a general formula:

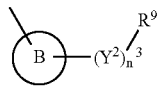

wherein $Y^2$ represents an alkylene group having from 1 to 6 carbon atoms of which the carbon chain may have a group selected from a sulfur atom, a sulfinyl group, a sulfonyl group, an oxygen atom, a carbonyl group, an oxycarbonyl group, a carbonyloxy group, and a group of a general formula:

wherein $R^7$ represents a hydrogen atom, an alkyl group having from 1 to 6 carbon atoms, a benzyl group, a phenyl group, a naphthyl group or a pyridyl group;

$n^3$ indicates 0 or 1;

$R^9$ represents a hydrogen atom, a halogen atom, a cyano group, an amino group, a nitro group, an alkyl group having from 1 to 10 carbon atoms, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, or an alkanoyl group having from 1 to 10 carbon atoms;

the group of a general formula:

means an aryl ring group or a heteroaryl ring group, in the presence of a palladium compound selected from a group consisting of palladium acetate, $Pd_2(dba)_3$ and $Pd(dba)_2$, a base selected from a group consisting of cesium carbonate, amine derivatives of a general formula:

wherein $R^3$, $R^4$ and $R^5$ may be the same or different, each representing an alkyl group having from 1 to 6 carbon atoms, a benzyl group, a phenyl group or a pyridyl group], 1,5-diazabicyclo[4.3.0]non-5-ene and 1,8-diazabicyclo[5.4.0]undec-7-ene, and a phosphorus compound selected from a group of a compound of a formula:

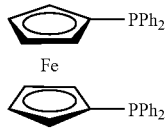

a compound of a formula:

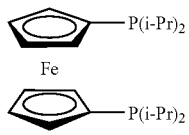

a compound of a formula:

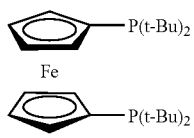

a compound of a formula:

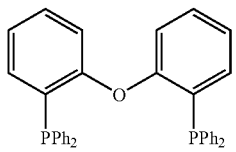

a compound of a formula:

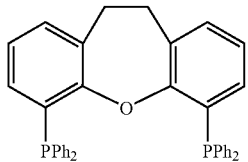

a compound of a formula:

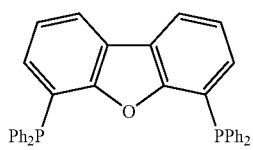

a compound of a formula:

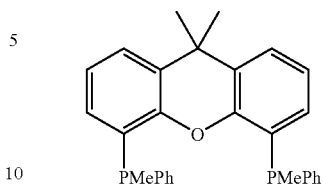

a compound of a formula:

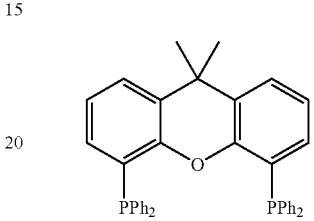

a compound of a formula:

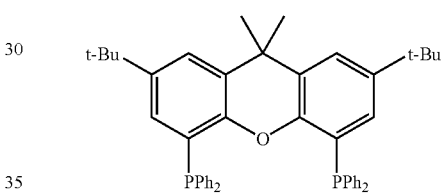

a compound of a formula:

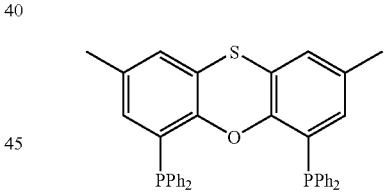

and a compound of a formula:

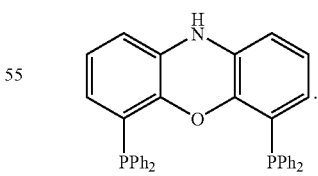

(2) The method for producing a thioether compound or its salt of (1), wherein the thiol compound of formula [II] is a thiol compound or its salt of a general formula [II-a]:

$$HS-R^e \qquad [II\text{-}a]$$

wherein $R^e$ represents a group of a general formula:

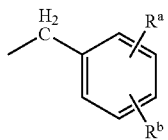

wherein $R^a$ and $R^b$ may be the same or different, each representing a hydrogen atom, an acetoxy group, a nitro group, or an alkoxy group having from 1 to 6 carbon atoms, a group of a general formula:

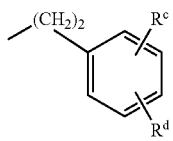

wherein $R^c$ and $R^d$ may be the same or different, each representing a hydrogen atom, a nitro group, or an alkoxy group having from 1 to 6 carbon atoms, or a group of a general formula:

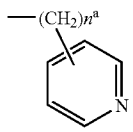

wherein $n^a$ indicates 1 or 2, or a (1-naphthyl)methyl group, a (2-naphthyl)methyl group, a 4-acetoxyphenyl group, a phenyl group, a trityl group, a diaminomethyl group, a 2-trimethylsilylethyl group or a 2-(2-ethylhexyloxycarbonyl)ethyl group].

(3) The method for producing a thioether compound or its salt of (2), wherein $R^e$ is a group of a general formula:

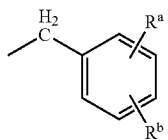

wherein $R^a$ and $R^b$ may be the same or different, each representing a hydrogen atom, an acetoxy group, a nitro group or an alkoxy group having from 1 to 6 carbon atoms, or a group of a general formula:

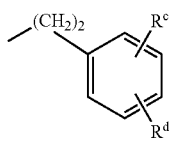

wherein $R^c$ and $R^d$ may be the same or different, each representing a hydrogen atom, a nitro group, or an alkoxy group having from 1 to 6 carbon atoms, or a group of a general formula:

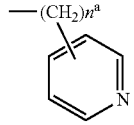

wherein $n^a$ indicates 1 or 2, or a (1-naphthyl)methyl group, or a (2-naphthyl)methyl group.

(4) The method for producing a thioether compound or its salt of (1), wherein the thiol compound of formula [II] is a thiol compound or its salt of a general formula:

[II-b]

wherein $R^f$ represents a 4-pyridylethyl group, a 4-methoxyphenyl group, a 4-pyridylmethyl group, a benzyl group, a 4-acetoxybenzyl group, a 4-nitrobenzyl group, a 4-acetoxyphenyl group, a phenyl group, a trityl group, a diaminomethyl group, a 2-trimethylsilylethyl group, or a 2-(2-ethylhexyloxycarbonyl)ethyl group.

(5) The method for producing a thioether compound or its salt of (1), wherein the palladium compound is $Pd_2(dba)_3$.

(6) The method for producing a thioether compound or its salt of (1), wherein the phosphorus compound is a compound of a formula:

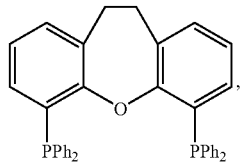

a compound of a formula:

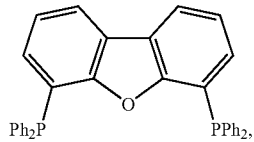

a compound of a formula:

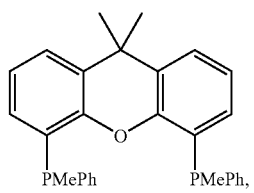

a compound of a formula:

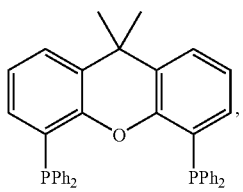

a compound of a formula:

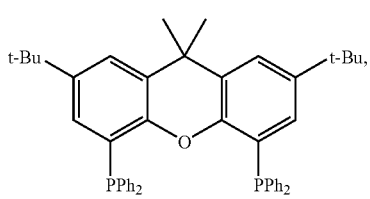

a compound of a formula:

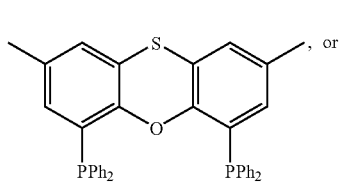, or a compound of a formula:

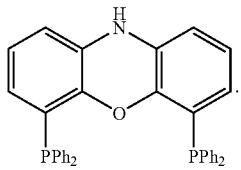

(7) The method for producing of (1), wherein the base is cesium carbonate, diisopropylethylamine, tributylamine, triethylamine, trimethylamine, dibenzylmethylamine, 4-dimethylaminopyridine, tribenzylamine, 1,5-diazabicyclo[4.3.0]non-5-ene, or 1,8-diazabicyclo[5.4.0]undec-7-ene.

(8) The method for producing a thioether compound or its salt of (1), wherein the base is diisopropylethylamine.

(9) The method for producing a thioether compound or its salt of (1), wherein the palladium compound is $Pd_2(dba)_3$, the phosphorus compound is a compound of a formula:

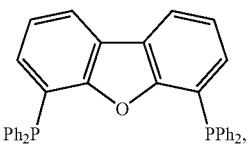

a compound of a formula:

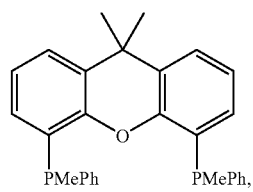

a compound of a formula:

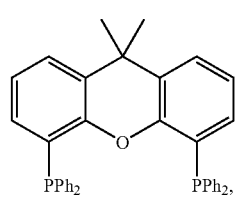

a compound of a formula:

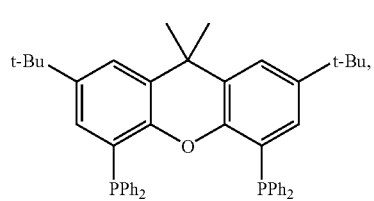

a compound of a formula:

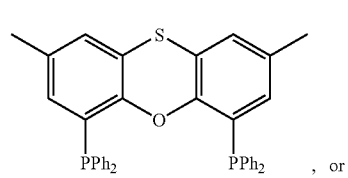, or a compound of a formula:

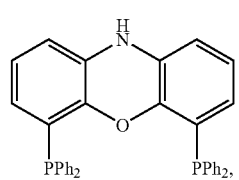

the base is cesium carbonate, diisopropylethylamine, tributylamine, triethylamine, dibenzylmethylamine, 1,5-diazabicyclo[4.3.0]non-5-ene, or 1,8-diazabicyclo[5.4.0]undec-7-ene.

(10) A method for producing a thiol compound or its salt of a general formula [I-b]:

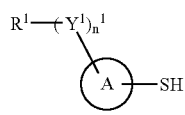
(I-b)

wherein $R^1$, $Y^1$, $n^1$ and the group of a general formula:

have the same meanings as mentioned below], which comprises reacting an aryl or heteroaryl compound or its salt of a general formula [III]:

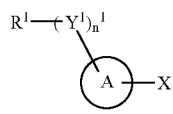
(III)

wherein $R^1$ represents a hydrogen atom, a halogen atom, a cyano group, an alkyl group having from 1 to 10 carbon atoms, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, or an alkanoyl group having from 1 to 10 carbon atoms;

$Y^1$ represents an alkylene group having from 1 to 6 carbon atoms of which the carbon chain may have a group selected from a sulfur atom, a sulfinyl group, a sulfonyl group, an oxygen atom, a carbonyl group, an oxycarbonyl group, a carbonyloxy group and a group of a general formula:

wherein $R^2$ represents a hydrogen atom, an alkyl group having from 1 to 6 carbon atoms, a benzyl group, a phenyl group, a naphthyl group or a pyridyl group;

X represents a bromine atom, a chlorine atom, a trifluoromethanesulfonyloxy group, a methylsulfonyloxy group, a benzenesulfonyloxy group, a toluenesulfonyloxy group or a nitrobenzenesulfonyloxy group;

$n^1$ indicates 0 or 1;

the group of a general formula:

means an aryl ring group or a heteroaryl ring group;

provided that when X is a chlorine atom, then the group of a general formula:

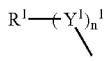

wherein $R^1$, $n^1$ and $Y^1$ have the same meanings as above] is an electron-withdrawing group, with a thiol compound or its salt of a general formula [II-a]:

$$HS—R^e \qquad [II\text{-}a]$$

wherein $R^e$ represents a group of a general formula:

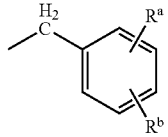

wherein $R^a$ and $R^b$ may be the same or different, each representing a hydrogen atom, an acetoxy group, a nitro group, or an alkoxy group having from 1 to 6 carbon atoms, a group of a general formula:

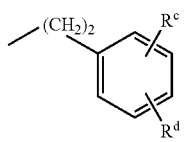

wherein $R^c$ and $R^d$ may be the same or different, each representing a hydrogen atom, a nitro group, or an alkoxy group having from 1 to 6 carbon atoms, or a group of a general formula:

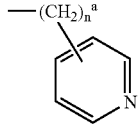

wherein $n^a$ indicates 1 or 2, or a (1-naphthyl)methyl group, a (2-naphthyl)methyl group, a 4-acetoxyphenyl group, a phenyl group, a trityl group, a diaminomethyl group, a 2-trimethylsilylethyl group or a 2-(2-ethylhexyloxycarbonyl)ethyl group, in the presence of a palladium compound selected from a group consisting of palladium acetate, Pd$_2$(dba)$_3$ and Pd(dba)$_2$, a base selected from a group consisting of cesium carbonate, amine derivatives of a general formula:

wherein R$^3$, R$^4$ and R$^5$ may be the same or different, each representing an alkyl group having from 1 to 6 carbon atoms, a benzyl group, a phenyl group or a pyridyl group, 1,5-diazabicyclo[4.3.0]non-5-ene and 1,8-diazabicyclo[5.4.0]undec-7-ene, and a phosphorus compound selected from a group of a compound of a formula:

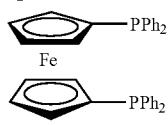

a compound of a formula:

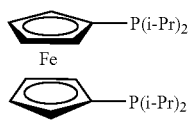

a compound of a formula:

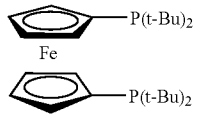

a compound of a formula:

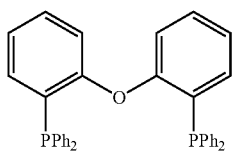

a compound of a formula:

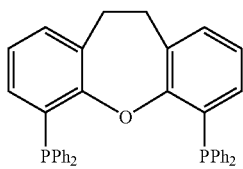

a compound of a formula:

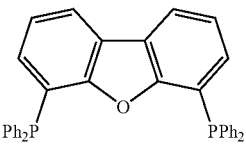

a compound of a formula:

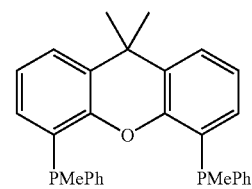

a compound of a formula:

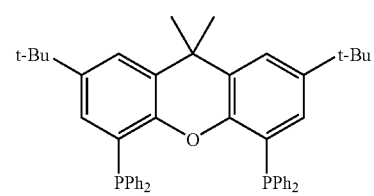

a compound of a formula:

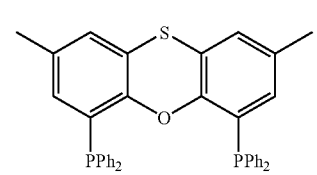

a compound of a formula:

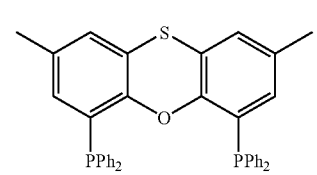

and a compound of a formula:

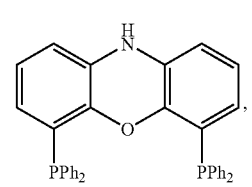

thereby affording a thioether compound or its salt of a general formula [I-a]:

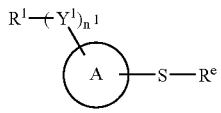

wherein $R^1$, $Y^1$, $R^e$, $n^1$ and the group of a general formula:

have the same meanings as above], and then removing the protective group of $R^e$ of the resulting thioether compound of formula [I-a].

(11) The method for producing of (1) or (10), wherein the alkylene group having from 1 to 6 carbon atoms, of which the carbon chain may have a group of a general formula:

wherein $R^7$ represents a hydrogen atom, an alkyl group having from 1 to 6 carbon atoms, a benzyl group, a phenyl group, a naphthyl group or a pyridyl group], is a methylene group, an ethylene group, a trimethylene group, a tetramethylene group, a pentamethylene group, a hexamethylene group, a propylene group, an ethylethylene group, or a group of a general formula:

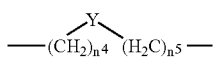

wherein Y represents a sulfur atom, a sulfinyl group, a sulfonyl group, an oxygen atom, a carbonyl group, an oxycarbonyl group, a carbonyloxy group, and a group of a general formula:

wherein $R^2$ represents a hydrogen atom, an alkyl group having from 1 to 6 carbon atoms, a benzyl group, a phenyl group, a naphthyl group or a pyridyl group; $n^4$ and $n^5$ each indicates an integer of from 1 to 6, and the sum of the two must not be more than 6.

(12) The method for producing of (1) or (10), wherein $n^1$ is 0.

(13) The method for producing of (1) or (10), wherein $n^2$ is 0.

(14) The method for producing of (1) or (10), wherein $n^3$ is 0.

(15) The method for producing for a thiol compound or its salt of (10), wherein the base is cesium carbonate, diisopropylethylamine, tributylamine, triethylamine, trimethylamine, dibenzylmethylamine, 4-dimethylaminopyridine, tribenzylamine, 1,5-diazabicyclo[4.3.0]non-5-ene, or 1,8-diazabicyclo[5.4.0]undec-7-ene.

(16) The method for producing a thiol compound or its salt of (10), wherein the palladium compound is $Pd_2(dba)_3$, the phosphorus compound is a compound of a formula:

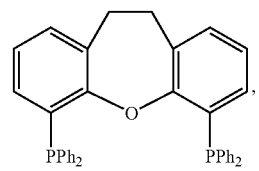

a compound of a formula:

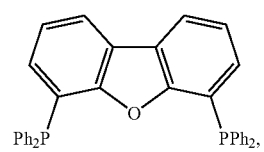

a compound of a formula:

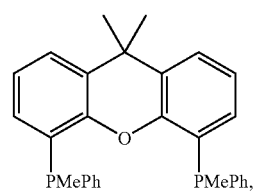

a compound of a formula:

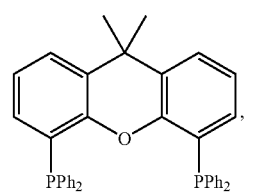

a compound of a formula:

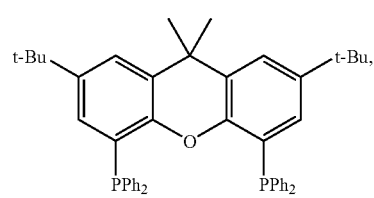

a compound of a formula:

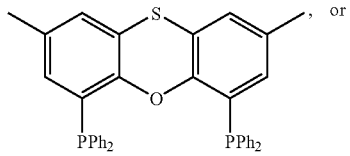, or a compound of a formula:

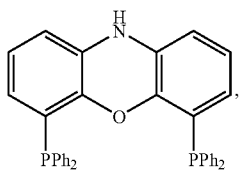

the base is cesium carbonate, diisopropylethylamine, tributylamine, triethylamine, trimethylamine, dibenzylmethylamine, 4-dimethylaminopyridine, tribenzylamine, 1,5-diazabicyclo[4.3.0]non-5-ene, or 1,8-diazabicyclo[5.4.0]undec-7-ene.

(17) The method for producing a thiol compound or its salt of (10), wherein the protective group of $R^e$ is a group of a general formula:

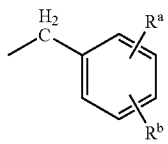

wherein $R^a$ and $R^b$ may be the same or different, each representing a hydrogen atom, an acetoxy group, a nitro group, or an alkoxy group having from 1 to 6 carbon atoms, a group of a general formula:

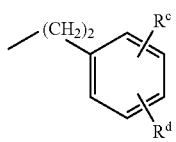

wherein $R^c$ and $R^d$ may be the same or different, each representing a hydrogen atom, a nitro group, or an alkoxy group having from 1 to 6 carbon atoms, a (1-naphthyl)methyl group, or a (2-naphthyl)methyl group.

(18) The method for producing a thiol compound or its salt of (10), wherein the protective group of $R^e$ is a phenethyl group of a general formula:

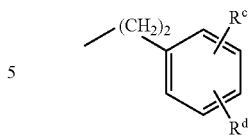

wherein $R^c$ and $R^d$ may be the same or different, each representing a hydrogen atom, a nitro group, or an alkoxy group having from 1 to 6 carbon atoms, and the step of removing the protective group of $R^e$ comprises treatment with a potassium alkoxide or a sodium alkoxide.

(19) The method for producing a thiol compound or its salt of (10), wherein the protective group of $R^e$ is a group of a general formula:

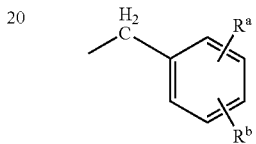

wherein $R^a$ and $R^b$ may be the same or different, each representing a hydrogen atom, an acetoxy group, a nitro group, or an alkoxy group having from 1 to 6 carbon atoms, a (1-naphthyl)methyl group or a (2-naphthyl)methyl group, and the step of removing the protective group of $R^e$ comprises treatment with a magnesium compound of a general formula:

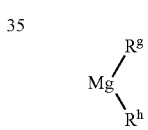

wherein $R^g$ represents a halogen atom, or an alkyl group having from 1 to 10 carbon atoms; $R^h$ represents an alkyl group having from 1 to 10 carbon atoms, in the presence of one additive selected from a group consisting of copper compounds, iron compounds, cobalt compounds, silver compounds, titanium compounds or their hydrates.

(20) The method for producing a thiol compound or its salt of (19), wherein the additive is $CuCl_2$, $CuCl_2 \cdot 2H_2O$, $FeCl_3$, $FeCl_2$, $TiCl_2(i\text{-}PrO)_2$, $Cu(CF_3SO_2O)_2$, $CoCl_2$, $AgNO_3$ or $Cp_2TiCl_2$.

(21) The method for producing a thiol compound or its salt of (19), wherein the magnesium compound is dimethylmagnesium, diethylmagnesium, di-n-butylmagnesium, di-n-propylmagnesium, n-butylmagnesium chloride, n-butylmagnesium bromide, methylmagnesium chloride, methylmagnesium bromide, ethylmagnesium chloride, ethylmagnesium bromide, n-propylmagnesium chloride, n-propylmagnesium bromide, isopropylmagnesium chloride or isopropylmagnesium bromide.

The symbols and the terms used in this description are described below, and the invention is described in more detail.

"Halogen atom" means a fluorine atom, a chlorine atom, a bromine atom, or an iodine atom.

"Alkyl group having from 1 to 6 carbon atoms" means a linear or branched alkyl group having from 1 to 6 carbon atoms, including, for example, a methyl group, an ethyl group, a n-propyl group, an isopropyl group, a n-butyl group, an isobutyl group, a sec-butyl group, a tert-butyl group, a pentyl group, an isopentyl group, a hexyl group, an isohexyl group.

"Alkyl group having from 1 to 10 carbon atoms" means a linear or branched alkyl group having from 1 to 10 carbon atoms, including, for example, a methyl group, an ethyl group, a n-propyl group, an isopropyl group, a n-butyl group, an isobutyl group, a sec-butyl group, a tert-butyl group, a pentyl group, an isopentyl group, a n-hexyl group, an isohexyl group, a 2-ethylhexyl group, a n-heptyl group, an isoheptyl group, a n-octyl group, an isooctyl group, a n-nonyl group, an isononyl group, a decyl group.

"Alkylene group having from 1 to 6 carbon atoms" means a linear or branched alkylene group having from 1 to 6 carbon atoms, including, for example, a methylene group, an ethylene group, a trimethylene group, a tetramethylene group, a pentamethylene group, a hexamethylene group, a propylene group, an ethylethylene group.

"Alkoxy group having from 1 to 6 carbon atoms" means a linear, branched or cyclic alkoxy group having from 1 to 6 carbon atoms, including, for example, a methoxy group, an ethoxy group, a n-propoxy group, an isopropoxy group, a n-butoxy group, an isobutoxy group a sec-butoxy group, a tert-butoxy group, a n-pentyloxy group, an isopentyloxy group, a cyclopentyloxy group, a hexyloxy group, an isohexyloxy group, a cyclohexyloxy group.

"Alkoxy group having from 1 to 10 carbon atoms" means a linear, branched or cyclic alkoxy group having from 1 to 10 carbon atoms, including, for example, a methoxy group, an ethoxy group, a n-propoxy group, an isopropoxy group, a n-butoxy group, an isobutoxy group a sec-butoxy group, a tert-butoxy group, a n-pentyloxy group, an isopentyloxy group, a cyclopentyloxy group, a hexyloxy group, an isohexyloxy group, a cyclohexyloxy group, a n-heptyloxy group, an isoheptyloxy group, a n-octyloxy group, an isooctyloxy group, a n-nonyloxy group, an isononyloxy group, a n-decanyloxy group, an isodecanyloxy group.

"Alkylthio group having from 1 to 10 carbon atoms" means a linear, branched or cyclic alkylthio group having from 1 to 10 carbon atoms, including, for example, a methylthio group, an ethylthio group, a n-propylthio group, an isopropylthio group, a n-butylthio group, an isobutylthio group, a sec-butylthio group, a tert-butylthio group, an n-pentylthio group, an isopentylthio group, a cyclopentylthio group, a n-hexylthio group, an isohexylthio group, a cyclohexylthio group, a n-heptylthio group, an isoheptylthio group, a n-octylthio group, an isooctylthio group, a n-nonylthio group, an isononylthio group, an n-decanylthio group, an iosdecanylthio group.

"Alkylsulfinyl group having from 1 to 10 carbon atoms" means a linear or branched alkylsulfinyl group having from 1 to 10 carbon atoms, including, for example, a methylsulfinyl group, an ethylsulfinyl group, a n-propylsulfinyl group, an isopropylsulfinyl group, a n-butylsulfinyl group, an isobutylsulfinyl group, a sec-butylsulfinyl group, a tert-butylsulfinyl group, an n-pentylsulfinyl group, an isopentylsulfinyl group, a n-hexylsulfinyl group, an isohexylsulfinyl group, a n-heptylsulfinyl group, an isoheptylsulfinyl group, a n-octylsulfinyl group, an isooctylsulfinyl group, a n-nonylsulfinyl group, an isononylsulfinyl group, an n-decanylsulfinyl group, an isodecanylsulfinyl group.

Alkylsulfonyl group having from 1 to 10 carbon atoms" means a linear, branched or cyclic alkylsulfonyl group having from 1 to 10 carbon atoms, including, for example, a methylsulfonyl group, an ethylsulfonyl group, a n-propylsulfonyl group, an isopropylsulfonyl group, a n-butylsulfonyl group, an isobutylsulfonyl group, a sec-butylsulfonyl group, a tert-butylsulfonyl group, an n-pentylsulfonyl group, an isopentylsulfonyl group, a cyclopentylsulfonyl group, a n-hexylsulfonyl group, an isohexylsulfonyl group, a cyclohexylsulfonyl group, a n-heptylsulfonyl group, an isoheptylsulfonyl group, a n-octylsulfonyl group, an isooctylsulfonyl group, a n-nonylsulfonyl group, an isononylsulfonyl group, an n-decanylsulfonyl group, an isodecanylsulfonyl group.

"Alkoxycarbonyl group having from 2 to 10 carbon atoms" means a linear, branched or cyclic alkoxycarbonyl group having from 2 to 10 carbon atoms, including, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a cyclopentyloxycarbonyl group, a hexyloxycarbonyl group, an isohexyloxycarbonyl group, a cyclohexyloxycarbonyl group, a n-heptyloxycarbonyl group, an isoheptyloxycarbonyl group, a n-octyloxycarbonyl group, an isooctyloxycarbonyl group, a n-nonyloxycarbonyl group, an isononyloxycarbonyl group.

"Alkanoyloxy group having from 2 to 10 carbon atoms" means a linear, branched or cyclic alkanoyloxy group having from 2 to 10 carbon atoms, including, for example, a formyloxy group, an acetoxy group, a propionyloxy group, a butyryloxy group, an isobutyryloxy group, a valeryloxy group, an isovaleryloxy group, a cyclopentylcarbonyloxy group, a pivaloyloxy group, a hexanoyloxy group, a cyclohexylcarbonyloxy group, a heptanoyloxy group, an octanoyloxy group, a nonanoyloxy group, a decanoyloxy group.

"Arylcarbonyl group" means an arylcarbonyl group including, for example, a benzoyl group, a 1-naphthylcarbonyl group, a 2-naphthylcarbonyl group.

"Arylcarbonyloxy group" means an arylcarbonyloxy group including, for example, a benzoyloxy group, a 1-naphthylcarbonyloxy group, a 2-naphthylcarbonyloxy group.

"Heteroarylcarbonyl group" means a heteroarylcarbonyl group including, for example, a 2-furylcarbonyl group, a 3-furylcarbonyl group, a 2-thienylcarbonyl group, a 3-thienylcarbonyl group, a 2-pyridylcarbonyl group, a 3-pyridylcarbonyl group, a 4-pyridylcarbonyl group, a 2-pyrrolylcarbonyl group, a 3-pyrrolylcarbonyl group, a 2-imidazolylcarbonyl group, a 4-imidazolylcarbonyl group, a 5-imidazolylcarbonyl group, a 3-pyrazolylcarbonyl group, a 4-pyrazolylcarbonyl group, a 5-pyrazolylcarbonyl group, a 2-pyrimidinylcarbonyl group, a 4-pyrimidinylcarbonyl group, a 5-pyrimidinylcarbonyl group, a 2-thiazolylcarbonyl group, a 2-oxazolylcarbonyl group, a 3-pyridazinyloxy group, a 2-pyradinylcarbonyl group, a 2-quinolylcarbonyl group, a 3-isoquinolyl group, 2-indolylcarbonyl group, a 1,8-naphthyridin-2-ylcarbonyl group.

"Heteroarylcarbonyloxy group" means a heteroarylcarbonyloxy group including, for example, a 2-furylcarbonyloxy group, a 3-furylcarbonyloxy group, a 2-thienylcarbonyloxy group, a 3-thienylcarbonyloxy group, a 2-pyridylcarbonyloxy group, a 3-pyridylcarbonyloxy group, a 4-pyridylcarbonyloxy group, a 2-pyrrolylcarbonyloxy group, a 3-pyrrolylcarbonyloxy group, a 2-imidazolylcarbonyloxy group, a 4-imidazolylcarbonyloxy group, a 5-imidazolylcarbonyloxy group, a 3-pyrazolylcarbonyloxy group, a 4-pyrazolylcarbonyloxy group, a 5-pyrazolylcarbonyloxy group, a 2-pyrimidinylcarbonyloxy group, a 4-pyrimidinylcarbonyloxy group, a 5-pyrimidinylcarbonyloxy group, a 2-thiazolylcarbonyloxy group, a 2-oxazolylcarbonyloxy group, a 3-pyridazinylcarbonyloxy group, a 2-pyradinylcarbonyloxy group, a 2-quinolylcarbonyloxy group, a 3-isoquinolylcarbonyloxy group, 2-indolylcarbonyloxy group, a 1,8-naphthyridin-2-ylcarbonyloxy group.

"Alkanoyl group having from 1 to 10 carbon atoms" means a linear, branched or cyclic alkanoyl group having from 1 to 10 carbon atoms, including, for example, a formyl group, an acetyl group, a propionyl group, a butyryl group, an isobutyryl group, a valeryl group, a cyclopentylcarbonyl group, an isovaleryl group, a pivaloyl group, a hexanoyl group, a cyclohexylcarbonyl group, a heptanoyl group, an octanoyl group, a nonanoyl group, a decanoyl group.

"Cycloalkyl group having from 3 to 8 carbon atoms" means a cycloalkyl group having from 3 to 8 carbon atoms, including, for example, a cyclopropyl group, a cyclobutyl group, a cyclopentyl group, a cyclohexyl group, a cycloheptyl group or a cyclooctyl group.

"Heteroarylcarbonylamino group" means a heteroarylcarbonylamino group including, for example, a 2-furylcarbonylamino group, a 3-furylcarbonylamino group, a 2-thienylcarbonylamino group, a 3-thienylcarbonylamino group, a 2-pyridylcarbonylamino group, a 3-pyridylcarbonylamino group, a 4-pyridylcarbonylamino group, a 2-pyrrolylcarbonylamino group, a 3-pyrrolylcarbonylamino group, a 2-imidazolylcarbonylamino group, a 4-imidazolylcarbonylamino group, a 5-imidazolylcarbonylamino group, a 3-pyrazolylcarbonylamino group, a 4-pyrazolylcarbonylamino group, a 5-pyrazolylcarbonylamino group, a 2-pyrimidinylcarbonylamino group, a 4-pyrimidinylcarbonylamino group, a 5-pyrimidinylcarbonylamino group, a 2-thiazolylcarbonylamino group, a 2-oxazolylcarbonylamino group, a 3-pyridazinylcarbonylamino group, a 2-pyrazinylcarbonylamino group, a 2-quinolylcarbonylamino group, a 3-isoquinolylcarbonylamino group, a 2-indolylcarbonylamino group, a 1,8-naphthyridin-2-ylcarbonylamino group.

"Arylcarbonylamino group" means an arylcarbonylamino group including, for example, a benzoylamino group, a 1-naphthylcarbonylamino group, a 2-naphthylcarbonylamino group.

"Alkanoylamino group having from 1 to 10 carbon atoms" means a linear or branched alkanoyl group having from 1 to 10 carbon atoms, including, for example, a formylamino group, an acetylamino group, a propionylamino group, a butyrylamino group, an isobutyrylamino group, a valerylamino group, an isovalerylamino group, a pivaloylamino group, a hexanoylamino group, a heptanoylamino group, an octanoylamino group, a nonanoylamino group, a decanoylamino group.

"Aryl group" means an aryl group including, for example, a phenyl group or a naphthyl group.

"Heteroaryl group" means a 5-membered or 6-membered, monocyclic aromatic heterocyclic group having 1 or more, preferably from 1 to 3, the same or different hetero atoms selected from a group consisting of an oxygen atom, a nitrogen atom and a sulfur atom, or a condensed ring-type aromatic heterocyclic group formed through condensation of the monocyclic aromatic heterocyclic group with the above-mentioned aryl group, or formed through condensation of the same or different, the above-mentioned monocyclic aromatic heterocyclic groups, and includes, for example, a pyrrolyl group, a furyl group, a thienyl group, a imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothie-nyl group, a benzimidazolyl group, a benzoxazolyl group, a benzisoxazolyl group, a benzo[1,3]dioxol group, dibenzofuranyl group, a thiaanthrenyl group, a benzothiazolyl group, a benzisothiazolyl group, a indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group.

"Aryl ring group" means "an aryl group substituted with two substituents".

"Heteroaryl ring group" means "a heteroaryl group substituted with two substituents".

"Alkanoyl group having from 1 to 6 carbon atoms" means a linear or branched alkanoyl group having from 1 to 6 carbon atoms, including, for example, an acetyl group, a propionyl group, a butyryl group, an isobutyryl group, a valeryl group, an isovaleryl group, a pivaloyl group.

"Aryloxy group" includes, for example, a phenoxy group, a 1-naphthyloxy group, a 2-naphthyloxy group.

"Alkylene group having from 1 to 6 carbon atoms of which the carbon chain may have a group selected from a sulfur atom, a sulfinyl group, a sulfonyl group, an oxygen atom, a carbonyl group, an oxycarbonyl group, a carbonyloxy group and a group of a general formula:

(wherein $R^2$ represents a hydrogen atom, an alkyl group having from 1 to 6 carbon atoms, a benzyl group, a phenyl group, a naphthyl group or a pyridyl group)" includes, for example, a methylene group, an ethylene group, a trimethylene group, a tetramethylene group, a pentamethylene group, a hexamethylene group, a propylene group, an ethylethylene group, or a group of a general formula:

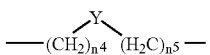

(wherein Y represents a sulfur atom, a sulfinyl group, a sulfonyl group, an oxygen atom, a carbonyl group, an oxycarbonyl group, a carbonyloxy group, and a group of a general formula:

(wherein $R^2$ represents a hydrogen atom, an alkyl group having from 1 to 6 carbon atoms, a benzyl group, a phenyl group, a naphthyl group or a pyridyl group); $n^4$ and $n^5$ each indicate an integer of from 1 to 6, and the sum of the two must not be more than 6).

"Electron-withdrawing group" means a group that attracts a ρ-electron or a π-electron in the molecule, such as a halogen atom, a nitro group, a carbonyl group, a carboxyl group, a cyano group, a sulfo group.

"Salt" means a salt formed by a functional group and an acid or a base. For example, a carboxyl group, a sulfo group or a thiol group forms a salt with an alkali metal salt such as sodium, potassium, lithium, or with an organic amine such as triethylamine, triethylamine. An amino group forms a salt with an acid such as hydrochloric acid, sulfuric acid, nitric acid; a thiol group forms a slat with an alkali metal such as sodium, potassium, lithium.

"dba" means dibenzylideneacetone.

"Ph" means a phenyl group.

"i-Pr" means an isopropyl group.

"Me" means a methyl group.

"t-Bu" means a tert-butyl group.

"Cp" means a cyclopentadienyl group.

The production method of the invention is described concretely hereinunder.

The method that comprises reacting an aryl or heteroaryl compound or its salt of a general formula [III]:

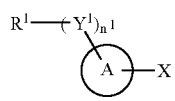
[III]

(wherein $R^1$ represents a hydrogen atom, a halogen atom, a cyano group, an alkyl group having from 1 to 10 carbon atoms, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, or an alkanoyl group having from 1 to 10 carbon atoms;

$Y^1$ represents an alkylene group having from 1 to 6 carbon atoms of which the carbon chain may have a group selected from a sulfur atom, a sulfinyl group, a sulfonyl group, an oxygen atom, a carbonyl group, an oxycarbonyl group, a carbonyloxy group and a group of a general formula:

(wherein $R^2$ represents a hydrogen atom, an alkyl group having from 1 to 6 carbon atoms, a benzyl group, a phenyl group, a naphthyl group or a pyridyl group);

X represents a bromine atom, a chlorine atom, a trifluoromethanesulfonyloxy group, a methylsulfonyloxy group, a benzenesulfonyloxy group, a toluenesulfonyloxy group or a nitrobenzenesulfonyloxy group;

$n^1$ indicates 0 or 1;

the group of a general formula:

means an aryl ring group or a heteroaryl ring group;

provided that when X is a chlorine atom, then the group of a general formula:

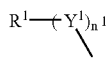

(wherein $R^1$, $n^1$ and $Y^1$ have the same meanings as above) is an electron-withdrawing group], with a thiol compound or its salt of a general formula [II]:

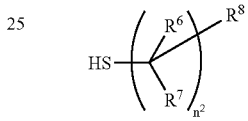
[II]

(wherein $R^6$ and $R^7$ may be the same or different, each representing a hydrogen atom, an alkyl group having from 1 to 6 carbon atoms, an amino group, or a phenyl group;

$n^2$ indicates from 0 to 6;

$R^8$ represents a hydrogen atom, a halogen atom, a cyano group, an amino group, an alkyl group having from 1 to 10 carbon atoms, a trimethylsilyl group, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, an alkanoyl group having from 1 to 10 carbon atoms, or a group of a general formula:

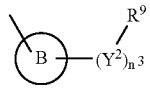

(wherein $Y^2$ represents an alkylene group having from 1 to 6 carbon atoms of which the carbon chain may have a group selected from a sulfur atom, a sulfinyl group, a sulfonyl group, an oxygen atom, a carbonyl group, an oxycarbonyl group, a carbonyloxy group, and a group of a general formula:

(wherein R⁷ represents a hydrogen atom, an alkyl group having from 1 to 6 carbon atoms, a benzyl group, a phenyl group, a naphthyl group or a pyridyl group);

n³ indicates 0 or 1;

R⁹ represents a hydrogen atom, a halogen atom, a cyano group, an amino group, a nitro group, an alkyl group having from 1 to 10 carbon atoms, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, or an alkanoyl group having from 1 to 10 carbon atoms);

the group of a general formula:

means an aryl ring group or a heteroaryl ring group), in the presence of a palladium compound selected from a group of palladium acetate, Pd₂(dba)₃ and Pd(dba)₂, a base selected from a group consisting of cesium carbonate, amine derivatives of a general formula:

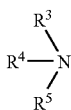

(wherein R³, R⁴ and R⁵ may be the same or different, each representing an alkyl group having from 1 to 6 carbon atoms, a benzyl group, a phenyl group or a pyridyl group), 1,5-diazabicyclo[4.3.0]non-5-ene and 1,8-diazabicyclo[5.4.0]undec-7-ene, and a phosphorus compound selected from a group of a compound (DPPF, 1,1'-bis(diphenylphosphino)ferrocene) of a formula:

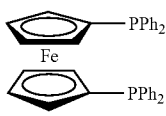

a compound (1,1'-bis(diisopropylphosphino)ferrocene) of a formula:

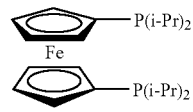

a compound (1,1'-bis(di-t-butylphosphino)ferrocene) of a formula:

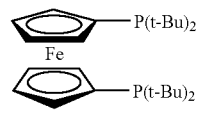

a compound (DPEphos) of a formula:

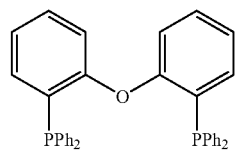

a compound (homoxantphos) of a formula:

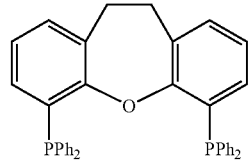

a compound (DEFphos) of a formula:

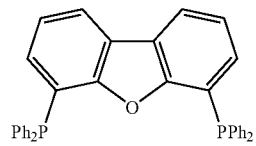

a compound (Xantphos) of a formula:

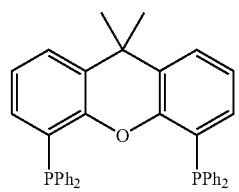

a compound (MeXantphos) of a formula:

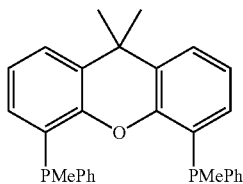

a compound (t-Bu-xantphos) of a formula:

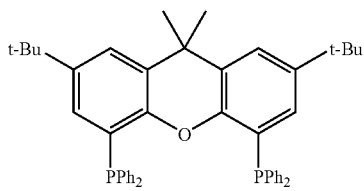

a compound (Thiaxantphos) of a formula:

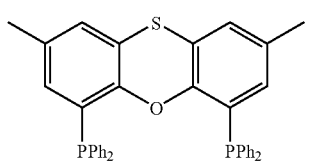

and a compound (Nixantphos) of a formula:

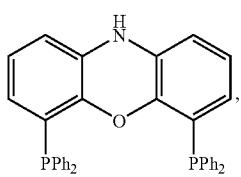

thereby producing a thioether compound or its salt of a general formula [I]:

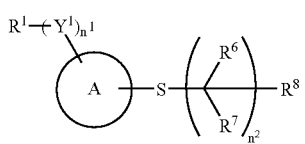

[I]

(wherein $R^1$, $Y^1$, $R^6$, $R^7$, $R^8$, $n^1$, $n^2$ and the group of a general formula:

have the same meanings as above] may be carried out by adding from 0.005 equivalents to 0.1 equivalents, relative to the aryl compound, the heteroaryl compound or its salt of formula [III], of the phosphorus compound, from 0.005 equivalents to 0.1 equivalents of the palladium compound, and from 1.5 equivalents to 2 equivalents of the base to a solvent not having any negative influence on the reaction, and reacting the compounds at 50° C. to 100° C. for 2 hours to 15 hours. The solvent not having any negative influence on the reaction includes, for example, dioxane, toluene, 2-methyltetrahydrofuran, tetrahydrofuran, N,N-dimethylformamide, dimethylimidazolidinone, N-methylpyrrolidone, dimethyl ether, diethyl ether.

The base includes cesium carbonate, amine derivatives of a general formula:

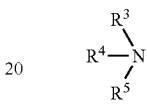

(wherein $R^3$, $R^4$ and $R^5$ may be the same or different, each representing an alkyl group having from 1 to 6 carbon atoms, a benzyl group, a phenyl group or a pyridyl group), 1,5-diazabicyclo[4.3.0]non-5-ene and 1,8-diazabicyclo[5.4.0]undec-7-ene.

The amine derivatives of a general formula:

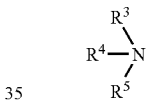

(wherein $R^3$, $R^4$ and $R^5$ may be the same or different, each representing an alkyl group having from 1 to 6 carbon atoms, a benzyl group, a phenyl group or a pyridyl group) include, for example, tertiary amines such as diisopropylethylamine, tributylamine, triethylamine, trimethylamine, dibenzylmethylamine, 4-dimethylaminopyridine or tribenzylamine.

The method that comprises producing a thioether compound or its salt of a general formula [I-a]:

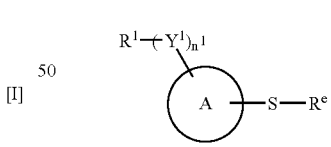

[I-a]

(wherein $R^1$, $Y^1$, $R^e$, $n^1$ and the group of a general formula:

have the same meanings as above), and then removing the protective group of $R^e$ from the resulting thioether compound of formula [I-a], thereby affording a thiol compound or its salt of a general formula [I-b]:

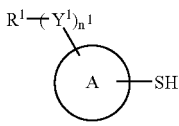

[I-b]

(wherein $R^1$, $Y^1$, $n^1$ and the group of a general formula:

have the same meanings as above) may be carried out according to the method of removing a substituent (protective group) bonding to a thiol group, as disclosed in the following known references, or according to a removing method similar to it.

Alan R. Katritzky, et al.; Tetrahedron Letters, vol. 25, No. 12, pp. 1223-1226 (1984).

Daniel A. Pearson, et al.; Tetrahedron Letters, Vol. 30, No. 21, pp. 2739-2742 (1989).

Constantinos G. Screttas, et al.; Tetrahedron Letters, Vol. 44, pp. 5633-5635 (2003).

Austin K. Flatt et al.; Tetrahedron Letters, Vol. 44, pp. 6699-6702 (2003).

Jean-Michel Becht, et al.; Journal of Organic Chemistry, Vol. 68, pp. 5758-5761 (2003).

Bulletin of the Chemical Society of Japan, Vol. 37, pp. 433-434 (1964).

However, when the protective group of $R^e$ is a group of a general formula:

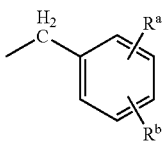

(wherein $R^a$ and $R^b$ may be the same or different, each representing a hydrogen atom, an acetoxy group, a nitro group, or an alkoxy group having from 1 to 6 carbon atoms), or a (1-naphthyl)methyl group or (2-naphthyl)methyl group, or when the protective group of $R^e$ is a group of a general formula:

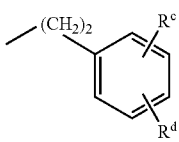

(wherein $R^a$ and $R^b$ may be the same or different, each representing a hydrogen atom, an acetoxy group, a nitro group, or an alkoxy group having from 1 to 6 carbon atoms), or a (1-naphthyl)methyl group or (2-naphthyl)methyl group, then the protective group of $R^e$ may be removed in a simplified and efficient manner according to the method which the present inventors have found out.

Specifically, when the protective group of $R^e$ is a group of a general formula:

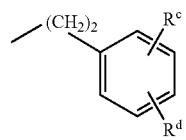

(wherein $R^c$ and $R^d$ may be the same or different, each representing a hydrogen atom, a nitro group, or an alkoxy group having from 1 to 6 carbon atoms), then the step of removing the protective group of $R^e$ may be attained through treatment with a potassium alkoxide or a sodium alkoxide in a solvent not having any negative influence on the reaction, by using from 1.5 to 5 equivalents, relative to one equivalent of the starting material, preferably from 2 to 3 equivalents of a potassium alkoxide or a sodium alkoxide, and processing the compound at −10° C. to 120° C. for 1 hour to 24 hours, preferably from 2 hours to 6 hours.

"Potassium alkoxide and sodium alkoxide" include, for example, potassium methoxide, potassium ethoxide, potassium n-propoxide, potassium isopropoxide, potassium n-butoxide, potassium isobutoxide, potassium t-butoxide, potassium n-pentoxide, potassium n-hexoxide, sodium methoxide, sodium ethoxide, sodium n-propoxide, sodium isopropoxide, sodium n-butoxide, sodium isobutoxide, sodium t-butoxide, sodium n-pentoxide, sodium n-hexoxide; preferably potassium n-butoxide, potassium isobutoxide, potassium t-butoxide, sodium n-butoxide, sodium isobutoxide, sodium t-butoxide.

"Solvent not having any negative influence on the reaction" to be used in this method includes diglyme, triglyme, tetraglyme, dimethylsulfoxide, 1,3-dimethyl-2-imidazolidinone, N-methylpyrrolidone, cyclopentyl methyl ether, 1,2-dimethoxyethane, N,N-dimethylformamide, N,N-dimethylacetamide; preferably diglyme, N,N-dimethylacetamide.

The group of a general formula:

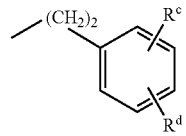

(wherein $R^c$ and $R^d$ may be the same or different, each representing a hydrogen atom, a nitro group, or an alkoxy group having from 1 to 6 carbon atoms) includes, for example, a phenethyl group, a 4-nitrophenethyl group, a 4-methoxyphenethyl group, a 2,4-dinitrophenethyl group or a 3,4-dimethoxyphenethyl group; preferably a phenethyl group.

When the protective group of $R^e$ is a group of a general formula:

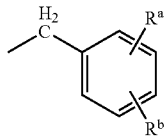

(wherein $R^a$ and $R^b$ may be the same or different, each representing a hydrogen atom, an acetoxy group, a nitro group, or an alkoxy group having from 1 to 6 carbon atoms), or a (1-naphthyl)methyl group or (2-naphthyl)methyl group, and when the removal of the protective group of $R^e$ is attained through treatment with a magnesium compound of a general formula:

(wherein $R^g$ represents a halogen atom, or an alkyl group having from 1 to 10 carbon atoms; $R^h$ represents an alkyl group having from 1 to 10 carbon atoms) in the presence of one additive selected from a group consisting of copper compounds, iron compounds, cobalt compounds, silver compounds and titanium compounds, then from 1.5 to 5 equivalents, relative to one equivalent of the starting material, preferably from 2 to 3 equivalents of the magnesium compound is used in the presence of from 0.05 to 1 equivalent, relative to 1 mol of the starting material, preferably from 0.05 to 0.5 equivalents of the additive, and the compound is processed in a solvent not having any negative influence on the reaction at −10° C. to 100° C., preferably at −10° C. to 50° C. for 1 hour to 36 hours, preferably for 2 hours to 24 hours.

The group of a general formula:

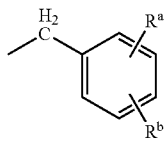

(wherein $R^a$ and $R^b$ may be the same or different, each representing a hydrogen atom, an acetoxy group, a nitro group, or an alkoxy group having from 1 to 6 carbon atoms) includes, for example, a benzyl group, a 4-nitrobenzyl group, a 4-methoxybenzyl group, a 2,4-dinitrobenzyl group, a 3,4-dimethoxybenzyl group, and is preferably a benzyl group.

"Solvent not having any negative influence on the reaction" for use in this method includes, for example, diglyme, triglyme, tetraglyme, ethyl ether, dioxane, methyltetrahydrofuran, tetrahydrofuran, methyl t-butyl ether, and is preferably diglyme.

"Additive" for use in this method includes, for example, $CuCl_2$, $CuCl_2 \cdot 2H_2O$, $FeCl_3$, $FeCl_2$, $TiCl_2(i\text{-PrO})_2$, $Cu(CF_3SO_2O)_2$, $CoCl_2$, $AgNO_3$, $Cp_2TiCl_2$ (wherein Cp means a cyclopentadienyl group); preferably, $CuCl_2$, $CuCl_2 \cdot 2H_2O$ or $Cp_2TiCl_2$.

"Magnesium compound" for use in this method includes, for example, dimethylmagnesium, diethylmagnesium, di-n-butylmagnesium, di-n-propylmagnesium, n-butylmagnesium chloride, n-butylmagnesium bromide, methylmagnesium chloride, methylmagnesium bromide, ethylmagnesium chloride, ethylmagnesium bromide, n-propylmagnesium chloride, n-propylmagnesium bromide, isopropylmagnesium chloride, isopropylmagnesium bromide; preferably di-n-butylmagnesium, n-butylmagnesium chloride, n-butylmagnesium bromide.

The products obtained in the above methods may be purified and isolated according to per-se known methods, for example, according to ordinary separation and isolation methods of column chromatography with silica gel or absorbent resin, liquid chromatography, thin-layer chromatography, solvent extraction, recrystallization or reprecipitation to be attained singly or optionally as combined.

The starting materials for the production methods of the invention may be commercially-available products or may be produced according to known production methods.

BEST MODE FOR CARRYING OUT THE INVENTION

The invention is described concretely with reference to the following Examples, by which, however, the invention should not be limited.

$Pd_2(dba)_3$ was bought from Johnson & Matthey. Xantphos was bought from Aldrich. Anhydrous $K_3PO_4$, anhydrous $K_2CO_3$, anhydrous $Na_2CO_3$ and anhydrous $Cs_2CO_3$ were bought from Wako Pure Chemicals. The other reagents used in the Examples were bought from Tokyo Kasei and Strem. Thiols, aryl halides, allyl trifluorosulfonate organic solvents were bought from Tokyo Kasei, and they were used after dried with Molecular Sieve (4 angstroms) and degassed.

All the reactions in the Examples were carried out in a dry nitrogen atmosphere, using a glass chamber dried with a drier.

For high-performance liquid chromatography, used was Hitachi's high-performance liquid chromatogram D-7000 (YMC basic reversed-phase column).

For column chromatography, used was EM silica gel 60 (particle size: 0.04 to 0.63 μm) as the carrier.

NMR data were determined with Bruker AV-500.

Example 1 to Example 27

According to the basic processes mentioned below, the compounds of Example 1 to Example 27 were produced.

(Basic Process)

An aryl halide or heteroaryl halide or aryl sulfonate, a base, a thiol compound and dry 1,4-dioxane are poured into a round-bottomed flask, and the round-bottomed flask with the resulting mixture therein is purged repeatedly three times with nitrogen gas, therefore having a nitrogen atmosphere therein. Next, as catalysts, $Pd_2(dba)_3$, Xantphos and a thiol compound are added to it, then this is purged repeatedly two times with nitrogen, and heated under reflux for 6 hours to 13 hours. Completion of the reaction is confirmed through high-performance liquid chromatography, then the resulting reaction solution is cooled to room temperature, the insoluble matter is taken out through filtration, and the filtrate is concentrated. The resulting concentrate is separated and purified through flash column chromatography with silica gel, therefore affording the thioether compound. If possible, this is purified through crystallization with a suitable solvent.

Example 1

Production of 4-methoxybenzyl phenyl sulfide

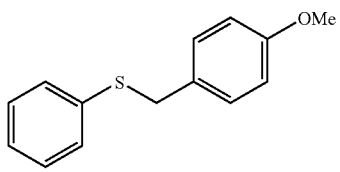

Heating and refluxing time: 6 hours.
Aryl halide and its amount used:
  Bromobenzene (211 μL, 2 mmol).
Thiol compound and its amount used:
  4-Methoxybenzylthiol (279 μL, 2 mmol).
Amount of $Pd_2(dba)_3$ used: 46 mg, 0.05 mmol.
Amount of Xantphos used: 58 mg, 0.1 mmol.
Base and its amount used:
  i-$Pr_2$NEt (700 μL, 4 mmol).
Amount of 1,4-dioxane used: 4.2 mL.
Property, yield and yield percentage of 4-methoxybenzyl phenyl sulfide:
  Pale yellow solid; yield 414 mg; yield percentage, 90%.
Development solvent in flash column chromatography:
  Hexane/ethyl acetate=5/1.
  Melting point: 79° C.-80° C.
  $^1$H NMR ($CDCl_3$, 500 MHz) δ ppm:
  7.17-7.31 (m, 7H), 6.81 (dt, 2H, J=2.1 Hz, 6.5 Hz), 4.07 (s, 2H), 3.77 (d, 3H, J=2.1 Hz).
  $^{13}$C NMR ($CDCl_3$, 125 MHz) δ ppm:
  159.18, 136.97, 130.34, 130.18, 129.80, 129.22, 126.66, 114.31, 55.66, 38.86.

Example 2

Production of diphenyl sulfide

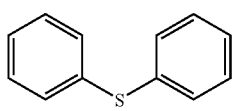

Heating and refluxing time: 6 hours.
Aryl halide and its amount used:
  Bromobenzene (211 μL, 2 mmol).
Thiol compound and its amount used:
  Thiophenol (205 μL, 2 mmol).
Amount of $Pd_2(dba)_3$ used: 46 mg, 0.05 mmol.
Amount of Xantphos used: 58 mg, 0.1 mmol.
Base and its amount used:
  i-$Pr_2$NEt (700 μL, 4 mmol)
Amount of 1,4-dioxane used: 4.2 mL. .
Property, yield and yield percentage of diphenyl sulfide:
  Colorless liquid; yield 316 mg; yield percentage, 85%.
Development solvent in flash column chromatography:
  Hexane.
  $^1$H NMR ($CDCl_3$, 500 MHz) δ ppm:
  7.21-7.35 (m, 10H).
  $^{13}$C NMR ($CDCl_3$, 125 MHz) δ ppm:
  136.21, 131.46, 129.60, 127.45.

Example 3

Production of 3-nitrophenyl phenyl sulfide

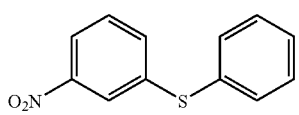

Heating and refluxing time: 6 hours.
Aryl halide and its amount used:
  3-Nitrobromobenzene (404 mg, 2 mmol).
Thiol compound and its amount used:
  Thiophenol (205 μL, 2 mmol).
Amount of $Pd_2(dba)_3$ used: 46 mg, 0.05 mmol.
Amount of Xantphos used: 58 mg, 0.1 mmol.
Base and its amount used:
  i-$Pr_2$NEt (700 μL, 4 mmol).
Amount of 1,4-dioxane used: 8.1 mL.
Property, yield and yield percentage of 3-nitrophenyl phenyl sulfide:
  Pale yellow liquid; yield 416 mg; yield percentage 90%.
Development solvent in flash column chromatography:
  Hexane/ethyl acetate=5/1.
  $^1$H NMR ($CDCl_3$, 500 MHz) δ ppm:
  7.99-8.04 (m, 4H), 7.47-7.51 (m, 3H), 7.39-7.43 (m, 2H).
  $^{13}$C NMR ($CDCl_3$, 125 MHz) δ ppm:
  134.26, 133.45, 132.14, 129.87, 129.68, 128.98, 128.96, 128.40, 123.17, 120.93.

Example 4

Production of 3-phenylsulfanylbenzaldehyde

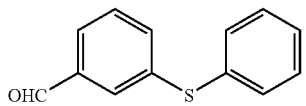

Heating and refluxing time: 6 hours.
Aryl halide and its amount used:
  3-Bromobenzaldehyde (233 μL, 2 mmol).
Thiol compound and its amount used:
  Thiophenol (205 μL, 2 mmol).
Amount of $Pd_2(dba)_3$ used: 46 mg, 0.05 mmol.

Amount of Xantphos used: 58 mg, 0.1 mmol.

Base and its amount used:
i-Pr$_2$NEt (700 μL, 4 mmol).

Amount of 1,4-dioxane used: 4.7 mL.

Property, yield and yield percentage of 3-phenylsulfanylbenzaldehyde:
Colorless liquid; yield 368 mg; yield percentage 86%.

Development solvent in flash column chromatography:
Hexane/ethyl acetate=15/1.
$^1$H NMR (CDCl$_3$, 500 MHz) δ ppm:
9.93 (s, 1H), 7.76 (dt, 1H, J=1.8 Hz), 7.69-7.71 (m, 1H), 7.50-7.52 (m, 1H), 7.42-7.45 (m, 3H), 7.26-7.38 (m, 3H).
$^{13}$C NMR (CDCl$_3$, 125 MHz) δ ppm:
192.16, 139.22, 137.52, 135.76, 134.03, 132.89, 131.03, 130.11, 129.98, 128.57, 128.03.

Example 5

Production of 4-phenylsulfanylacetophenone

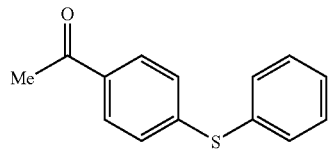

Heating and refluxing time: 6 hours.

Aryl halide and its amount used:
4-Bromoacetophenone (398 mg, 2 mmol).

Thiol compound and its amount used:
Thiophenol (205 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μL, 4 mmol).

Amount of 1,4-dioxane used: 8 mL.

Property, yield and yield percentage of 4-phenylsulfanylacetophenone:
White solid; yield 411 mg; yield percentage 90%.

Development solvent in flash column chromatography:
Hexane/ethyl acetate=10/1.

Melting point: 66° C.-67° C.
$^1$H NMR (CDCl$_3$, 500 MHz) δ ppm:
7.82 (dt, 2H, J=1.8 Hz, 6.7 Hz), 7.50 (dt, 2H, J=1.8 Hz, 7.8 Hz), 7.38-7.42 (m, 3H), 7.21 (dt, 2H, J=1.8 Hz, 6.7 Hz), 2.55 (s, 3H).
$^{13}$C NMR (CDCl$_3$, 125 MHz) δ ppm:
197.13, 144, 92, 134.52, 133.87, 132.13, 129.69, 128.90, 128.80, 127.50, 26.47.

Example 6

Production of 4-phenylsulfanylanisole

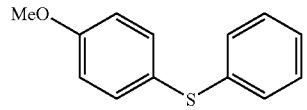

Heating and refluxing time: 15 hours.

Aryl halide and its amount used:
4-Bromoanisole (250 μL, 2 mmol).

Thiol compound and its amount used:
Thiophenol (205 μL, 2 mmol).

Amount of Pd$_2$(dba)$_3$ used: 46 mg, 0.05 mmol.

Amount of Xantphos used: 58 mg, 0.1 mmol.

Base and its amount used:
Cs$_2$CO$_3$ (652 mg, 4 mmol).

Amount of 1,4-dioxane used: 5 mL.

Property, yield and yield percentage of 4-phenylsulfanylanisole:
Pale yellow liquid; yield 311 mg; yield percentage 72%.

Development solvent in flash column chromatography:
Hexane/ethyl acetate=15/1.
$^1$H NMR (500 MHz, DMSO) δ ppm:
7.41 (dt, 2H, J=2.1 Hz, 6.8 Hz), 7.13-7.24 (m, 5H), 6.89 (dt, 2H, J=2.1 Hz, 6.8 Hz), 3.81 (s, 3H).
$^{13}$C NMR (CDCl$_3$, 125 MHz) δ ppm:
160.25, 139.01, 135.76, 129.33, 128.64, 126.18, 124.75, 115.40, 55.77.

Example 7

Production of 4-(4-methoxyphenyl)sulfanylanisole

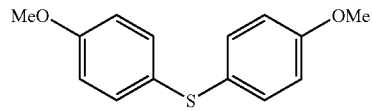

Heating and refluxing time: 8 hours.

Aryl halide and its amount used:
4-Bromoanisole (250 μL, 2 mmol).

Thiol compound and its amount used:
4-Methoxythiophenol (246 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μl, 4 mmol).

Amount of 1,4-dioxane used: 8.1 mL.

Property, yield and yield percentage of 4-(4-methoxyphenyl)sulfanylanisole:
Pale yellow liquid; yield 389 mg; yield percentage 79%.

Development solvent in flash column chromatography:
Hexane/ethyl acetate=5/1.
$^1$H NMR (CDCl$_3$, 500 MHz) δ ppm
7.27 (dd, 4H, J=2.1 Hz, 6.7 Hz), 6.83 (dd, 4H, J=2.1 Hz, 6.8 Hz), 3.78 (s, 6H).
$^{13}$C NMR (CDCl$_3$, 125 MHz) δ ppm:
158.99, 132.73, 127.45, 114.76, 55.35.

Example 8

Production of 2-tolyl phenyl sulfide

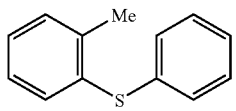

Heating and refluxing time: 7 hours.

Aryl halide and its amount used:
2-Bromotoluene (241 μL, 2 mmol).

Thiol compound and its amount used:
Thiophenol (205 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μl, 4 mmol).

Amount of 1,4-dioxane used: 4.8 mL.

Property of 2-tolyl phenyl sulfide:
Pale yellow liquid.

Development solvent in flash column chromatography:
Hexane/ethyl acetate=15/1.
$^1$H NMR (500 MHz, DMSO) δ ppm:
7.19-7.29 (m, 9H), 2.38 (s, 3H).
$^{13}$C NMR (CDCl$_3$, 125 MHz) δ ppm:
133.43, 131.01, 130.05, 129.54, 129.48, 128.32, 127.95, 127.57, 127.13, 126.75, 21.00.

Example 9

Production of 2-isopropylphenyl phenyl sulfide

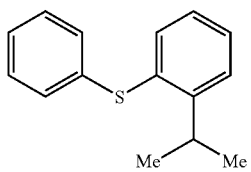

Heating and refluxing time: 6 hours.

Aryl halide and its amount used:
Bromobenzene (211 μL, 2 mmol).

Thiol compound and its amount used:
2-Isopropylbenzenethiol (303 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μl, 4 mmol).

Amount of 1,4-dioxane used: 4.2 mL.

Property, yield and yield percentage of isopropyl phenyl sulfide:
Colorless liquid; yield 402 mg; yield percentage 88%.

Development solvent in flash column chromatography:
Hexane/ethyl acetate=10/1.
$^1$H NMR (CDCl$_3$, 500 MHz) δ ppm:
7.11-7.36 (m, 9H), 3.56 (hept, 1H, J=6.9 Hz), 1.21 (d, 6H, J=6.9 Hz).
$^{13}$C NMR (CDCl$_3$, 125 MHz) δ ppm:
150.51, 137.37, 133.93, 132.50, 129.36, 129.04, 128.46, 126.58, 126.11, 126.09, 30.64, 23.54.

Example 10

Production of 5-(2'-isopropylphenylsulfanyl)-2-methylpyridine

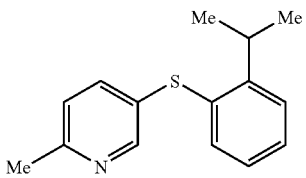

Heating and refluxing time: 6 hours.

Heteroaryl halide and its amount used:
5-Bromo-2-methylpyridine (344 mg, 2 mmol).

Thiol compound and its amount used:
2-Isopropylbenzenethiol (303 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μl, 4 mmol).

Amount of 1,4-dioxane used: 7.0 mL.

Property, yield and yield percentage of 5-(2'-isopropylphenylsulfanyl)-2-methylpyridine:
Colorless liquid; yield 443 mg; yield percentage 91%.

Development solvent in flash column chromatography:
Hexane/ethyl acetate=15/1.
$^1$H NMR (CDCl$_3$, 500 MHz) δ ppm:
8.39 (d, 1H, J=2.3 Hz), 7.40 (dt, 1H, J=2.4 Hz, 8.1 Hz), 7.34 (dt, 1H, J=1.4 Hz, 7.8 Hz), 7.26-7.29 (m, 1H), 7.21 (dt, 1H, J=1.4 Hz, 7.8 Hz), 7.05-7.12 (m, 2H), 3.54 (hept, 1H, J=6.9 Hz), 2.52 (s, 3H), 1.22 (d, 6H, J=6.9 Hz).
$^{13}$C NMR (CDCl$_3$, 125 MHz) δ ppm:
156.62, 150.29, 149.87, 138.16, 132.90, 132.27, 130.43, 128.40, 126.72, 126.16, 123.62, 30.65, 23.99, 23.49.

Example 11

Production of 5-phenylsulfanylindole

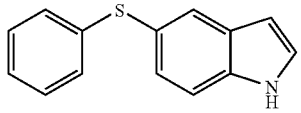

Heating and refluxing time: 6 hours.

Heteroaryl halide and its amount used:
  5-Bromoindole (392 μL, 2 mmol).

Thiol compound and its amount used:
  Thiophenol (205 μL, 2 mmol).

Amount of $Pd_2(dba)_3$ used: 46 mg, 0.05 mmol.

Amount of Xantphos used: 58 mg, 0.1 mmol.

Base and its amount used:
  i-$Pr_2$NEt (700 μl, 4 mmol).

Amount of 1,4-dioxane used: 8.0 mL.

Property, yield and yield percentage of 5-phenylsulfanylindole:
  White solid; yield 405 mg; yield percentage 90%.

Development solvent in flash column chromatography:
  Hexane/ethyl acetate=10/1.

Melting point: 98° C.-99° C.
  $^1$H NMR ($CDCl_3$, 500 MHz) δ ppm:
  8.18 (bs, 1H), 7.85 (d, 1H, J=0.8 Hz), 7.31-7.36 (m, 2H), 7.15-7.23 (m, 5H), 7.07-7.11 (m, 1H), 6.53 (dd, 1H, J=0.8 Hz, 2.1 Hz).
  $^{13}$C NMR ($CDCl_3$, 125 MHz) δ ppm:
  8.140.12, 136.08, 129.31, 129.23, 128.64, 128.14, 127.77, 125.76, 125.55, 12.

Example 12

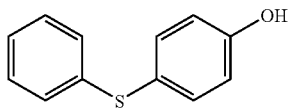

Heating and refluxing time: 8 hours.

Aryl halide and its amount used:
  Bromobenzene (211 μL, 2 mmol).

Thiol compound and its amount used:
  4-Mercaptothiol (252 mg, 2 mmol).

Amount of $Pd_2(dba)_3$ used: 46 mg, 0.05 mmol.

Amount of Xantphos used: 58 mg, 0.1 mmol.

Base and its amount used:
  i-$Pr_2$NEt (700 μl, 4 mmol).

Amount of 1,4-dioxane used: 4.2 mL.

Property, yield and yield percentage of 4-phenylsulfanylphenol:
  Colorless liquid; yield 356 mg; yield percentage 88%.

Development solvent in flash column chromatography:
  Hexane/ethyl acetate=10/1.
  $^1$H NMR ($CDCl_3$, 500 MHz) δ ppm:
  7.36 (dt, 2H, J=2.1 Hz, 6.7 Hz), 7.22-7.25 (m, 2H), 7.12-7.18 (m, 3H), 6.81 (dt, 2H, J=2.1 Hz, 6.7 Hz), 5.18 (bs, 1H).
  $^{13}$C NMR ($CDCl_3$, 125 MHz) δ ppm:
  155.81, 138.36, 135.49, 128.96, 128.35, 125.88, 124.66, 116.49.

Example 13

Production of cyclohexyl phenyl sulfide

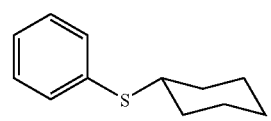

Heating and refluxing time: 13 hours.

Aryl halide and its amount used:
  Bromobenzene (211 μL, 2 mmol).

Thiol compound and its amount used:
  Cyclohexylmercaptan (245 μL, 2 mmol).

Amount of $Pd_2(dba)_3$ used: 46 mg, 0.05 mmol.

Amount of Xantphos used: 58 mg, 0.1 mmol.

Base and its amount used:
  i-$Pr_2$NEt (700 μl, 4 mmol).

Amount of 1,4-dioxane used: 4.2 mL.

Property, yield and yield percentage of cyclohexyl phenyl sulfide:
  Colorless liquid; yield 308 mg; yield percentage 80%.

Development solvent in flash column chromatography:
  Hexane/ethyl acetate=10/1.
  $^1$H NMR ($CDCl_3$, 500 MHz) δ ppm:
  7.38-7.40 (m, 2H), 7.26-7.29 (m, 2H), 7.19-7.22 (m, 1H), 3.07-3.13 (m, 1H), 1.97-2.00 (m, 2H), 1.75-1.79 (m, 2H), 1.60-1.63 (m, 1H), 1.23-1.41 (m, 5H).
  $^{13}$C NMR ($CDCl_3$, 125 MHz) δ ppm:
  135.58, 132.27, 129.13, 126.97, 46.98, 33.75, 26.46, 26.17.

Example 14

Production of benzyl phenyl sulfide

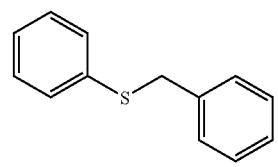

Heating and refluxing time: 8 hours.

Aryl halide and its amount used:
  Bromobenzene (211 μL, 2 mmol).

Thiol compound and its amount used:
  Benzylmercaptan (235 μL, 2 mmol).

Amount of Pd$_2$(dba)$_3$ used: 46 mg, 0.05 mmol.

Amount of Xantphos used: 58 mg, 0.1 mmol.

Base and its amount used:
  i-Pr$_2$NEt (700 μl, 4 mmol).

Amount of 1,4-dioxane used: 4.2 mL.

Property, yield and yield percentage of benzyl phenyl sulfide:
  Yellow solid; yield 368 mg; yield percentage 92%.

Development solvent in flash column chromatography:
  Hexane/ethyl acetate=15/1.
  Melting point: 40° C.-41° C.
  $^1$H NMR (CDCl$_3$, 500 MHz) δ ppm:
  7.16-7.31 (m, 10H), 4.10 (s, 2H).
  $^{13}$C NMR (CDCl$_3$, 500 MHz) δ ppm:
  137.89, 136.80, 130.26, 129.25, 128.90, 127.59, 126.76, 39.48.

Example 15

Production of phenyl 2-(4-pyridyl)ethyl sulfide

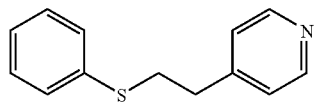

Heating and refluxing time: 6 hours.

Aryl halide and its amount used:
  Bromobenzene (211 μL, 2 mmol).

Thiol compound and its amount used:
  4-Pyridinethanethiol hydrochloride (351 mg, 2 mmol).

Amount of Pd$_2$(dba)$_3$ used: 46 mg, 0.05 mmol.

Amount of Xantphos used: 58 mg, 0.1 mmol.

Base and its amount used:
  i-Pr$_2$NEt (1.05 mL, 6 mmol).

Amount of 1,4-dioxane used: 4.2 mL.

Property, yield and yield percentage of phenyl 2-(4-pyridyl)ethyl sulfide:
  Pale yellow liquid; yield 396 mg; yield percentage 92%.

Development solvent in flash column chromatography:
  Hexane/ethyl acetate=5/1.
  $^1$H NMR (CDCl$_3$, 500 MHz) δ ppm:
  8.51 (d, 1H, J=1.6 Hz), 8.50 (d, 1H, J=1.6 Hz), 7.29-7.37 (m, 4H), 7.20-7.23 (m, 1H), 7.11 (d, 2H, J=6.0 Hz), 3.17 (dt, 2H, J=7.3 Hz, 8.0 Hz), 2.91 (dt, 2H, J=7.3 Hz, 8.0 Hz).
  $^{13}$C NMR (CDCl$_3$, 125 MHz) δ ppm:
  150.28, 149.26, 135.98, 130.17, 129.46, 126.87, 124.29, 35.23, 34.52.

Example 16

Production of 2-ethylhexyl 3-phenylsulfanylpropionate

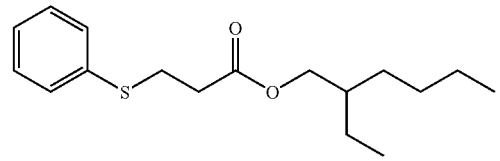

Heating and refluxing time: 6 hours.

Aryl halide and its amount used:
  Bromobenzene (211 μL, 2 mmol).

Thiol compound and its amount used:
  2-Ethylhexyl 3-mercaptopropionate (460 μL, 2 mmol).

Amount of Pd$_2$(dba)$_3$ used: 46 mg, 0.05 mmol.

Amount of Xantphos used: 58 mg, 0.1 mmol.

Base and its amount used:
  i-Pr$_2$NEt (700 μL, 4 mmol).

Amount of 1,4-dioxane used: 4.2 mL.

Property, yield and yield percentage of 2-ethylhexyl 3-phenylsulfanylpropionate:
  Colorless liquid; yield 518 mg; yield percentage 88%.

Development solvent in flash column chromatography:
  Hexane.
  $^1$H NMR (CDCl$_3$, 500 MHz) δ ppm:
  7.35-7.38 (m, 2H), 7.31-7.28 (m, 2H), 7.19-7.23 (m, 1H), 4.01 (dd, 2H, J=2.7 Hz, 5.7 Hz), 3.17 (dd, 2H, J=4.3 Hz, 7.4 Hz), 2.63 (dd, 2H, J=4.3 Hz, 7.4 Hz), 1.57 (m, 1H), 1.36 (m, 2H), 1.30 (m, 6H), 0.87-0.90 (m, 6H).
  $^{13}$C NMR (CDCl$_3$, 125 MHz) δ ppm:
  171.92, 135.32, 130.07, 129.02, 126.54, 67.21, 38.73, 34.49, 30.41, 29.14, 28.92, 23.79, 22.97, 14.05, 11.00.

Example 17

Production of 5-(4-methoxybenzylsulfanyl)-2-methylpyridine

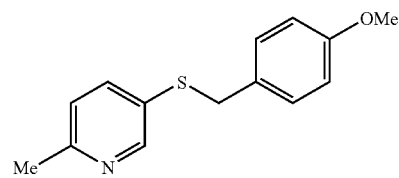

Heating and refluxing time: 7 hours.

Aryl halide and its amount used:
  5-Bromo-2-methylpyridine (344 mg, 2 mmol).

Thiol compound and its amount used:
  4-Methoxyphenylmercaptan (279 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μL, 4 mmol).

Amount of 1,4-dioxane used: 13.8 mL.

Property, yield and yield percentage of 5-(4-methoxybenzyl-sulfanyl)-2-methylpyridine:
White solid; yield 417 mg; yield percentage 85%.

Development solvent in flash column chromatography:
Hexane/ethyl acetate=2/1.
Melting point: 59° C.-60° C.
$^1$H NMR (CDCl$_3$, 500 MHz) δ ppm:
8.41 (d, 1H, J=2.2 Hz), 7.45 (dt, 1H, J=2.4 Hz, 8.1 Hz), 7.13 (dt, 2H, J=2.0 Hz, 6.7 Hz), 7.02 (d, 1H, J=8.1 Hz), 6.80 (dt, 2H, J=2.0 Hz, 6.7 Hz), 4.00 (s, 2H), 3.78 (s, 3H), 2.51 (s, 3H).
$^{13}$C NMR (CDCl$_3$, 125 MHz) δ ppm:
159.25, 157.34, 151.78, 139.85, 130.37, 129.56, 123.59, 114.34, 55.64, 39.81, 24.42.

Example 18

Production of 2-methyl-5-phenethylsulfanylpyridine

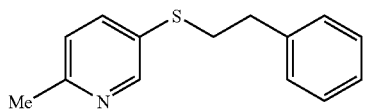

Heating and refluxing time: 6 hours.

Aryl halide and its amount used:
5-Bromo-2-methylpyridine (344 mg, 2 mmol).

Thiol compound and its amount used:
Benzenethanethiol (268 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μL, 4 mmol).

Amount of 1,4-dioxane used: 6.9 mL.

Property, yield and yield percentage of 2-methyl-5-phenethylsulfanylpyridine:
Pale yellow liquid; yield 381 mg; yield percentage 83%.

Development solvent in flash column chromatography:
Hexane/ethyl acetate=5/1.
$^1$H NMR (CDCl$_3$, 500 MHz) δ ppm:
8.50 (d, 1H, J=2.3 Hz), 7.57 (dt, 1H, J=2.4 Hz, 8.1 Hz), 7.29 (dd, 2H, J=7.1 Hz, 7.6 Hz), 7.22 (dt, 1H, J=1.2 Hz, 7.6 Hz), 7.17 (dd, 2H, J=1.2 Hz, 7.1 Hz), 7.08 (d, 1H, J=8.1 Hz), 3.12 (dd, 2H, J=7.5 Hz, 8.1 Hz), 2.89 (dd, 2H, J=7.5 Hz, 8.1 Hz), 2.53 (s, 3H).
$^{13}$C NMR (CDCl$_3$, 125 MHz) δ ppm:
156.61, 150.62, 139.78, 138.53, 129.52, 128.55, 128.51, 126.55, 123.38, 36.06, 35.78, 23.98.

Example 19

Production of 4-nitrophenyl phenyl sulfide

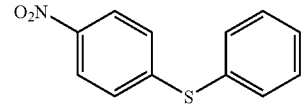

Heating and refluxing time: 7 hours.

Aryl sulfonate and its amount used:
4-Nitrobenzene trifluoromethanesulfonate (542 mg, 2 mmol).

Thiol compound and its amount used:
Thiophenol (205 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μL, 4 mmol).

Amount of 1,4-dioxane used: 10.8 mL.

Property, yield and yield percentage of 4-nitrophenyl phenyl sulfide:
Pale yellow solid; yield 425 mg; yield percentage 92%.

Development solvent in flash column chromatography:
Hexane/ethyl acetate=10/1.
Melting point: 54° C.-55° C.
$^1$H NMR (CDCl$_3$, 500 MHz) δ ppm:
8.06 (dt, 2H, J=2.0 Hz, 7.0 Hz), 7.53-7.55 (m, 2H), 7.46 (d, 2H, J=2.4 Hz), 7.45 (d, 1H, J=1.0 Hz), 7.18 (dt, 2H, J=2.0 Hz, 7.0 Hz).
$^{13}$C NMR (CDCl$_3$, 125 MHz) δ ppm:
148.90, 145.78, 135.15, 130.88, 130.44, 130.07, 127.11, 124.44.

Example 20

Production of 4-tolyl phenyl sulfide

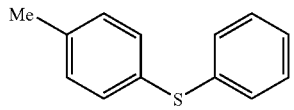

Heating and refluxing time: 15 hours.

Aryl sulfonate and its amount used:
4-Tolyl trifluoromethanesulfonate (358 μL, 2 mmol).

Thiol compound and its amount used:
Thiophenol (205 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μL, 4 mmol).

Amount of 1,4-dioxane used: 7.2 mL.

Property, yield and yield percentage of 4-tolyl phenyl sulfide:
Pale yellow oil; yield 316 mg; yield percentage 79%.

Development solvent in flash column chromatography:
Hexane/ethyl acetate=5/1.
$^1$H NMR (500 MHz) δ ppm:
7.45-6.90 (m, Ar—H), 2.26 (s, 3H, CH$_3$).
$^{13}$C NMR (CDCl$_3$, 125 MHz) δ ppm:
137.52, 136.98, 132.09, 131.20, 130.10, 129.68, 128.89, 126.33, 21.05.

Example 21

Production of diphenyl sulfide

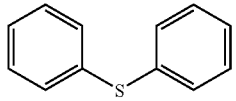

Heating and refluxing time: 6 hours.

Aryl sulfonate and its amount used:
Benzene trifluorosulfonate (324 μL, 2 mmol).

Thiol compound and its amount used:
Thiophenol (205 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μL, 4 mmol).

Amount of 1,4-dioxane used: 6.5 mL.

Property, yield and yield percentage of diphenyl sulfide:
Colorless liquid; yield 335 mg; yield percentage 90%.

Development solvent in flash column chromatography:
Hexane.
$^1$H NMR (CDCl$_3$, 500 MHz) δ ppm:
7.21-7.35 (m, 10H).
$^{13}$C NMR (CDCl$_3$, 125 MHz) δ ppm:
136.21, 131.46, 129.60, 127.45.

Example 22

Production of 1-naphthyl phenyl sulfide

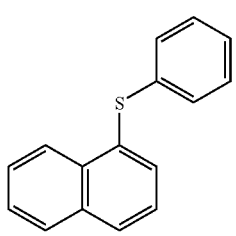

Heating and refluxing time: 7 hours.

Aryl sulfonate and its amount used:
1-Naphthyl trifluoromethanesulfonate (393 μL, 2 mmol).

Thiol compound and its amount used:
Thiophenol (205 μL, 2 mmol).

Amount of Pd$_2$(dba)$_3$ used: 46 mg, 0.05 mmol.

Amount of Xantphos used: 58 mg, 0.1 mmol.

Base and its amount used:
i-Pr$_2$NEt (700 μL, 4 mmol).

Amount of 1,4-dioxane used: 7.9 mL.

Property, yield and yield percentage of 1-naphthyl phenyl sulfide:
Colorless liquid; yield 435 mg; yield percentage 92%.

Development solvent in flash column chromatography:
Hexane.
$^1$H NMR (500 MHz) δ ppm:
8.37-8.39 (m, 1H), 7.83-7.87 (m, 2H), 7.66 (dt, 1H, J=1.1 Hz, 7.2 Hz), 7.49-7.52 (m, 2H), 7.41 (dd, 1H, J=7.2 Hz, 8.2 Hz), 7.14-7.22 (m, 5H).
$^{13}$C NMR (CDCl$_3$, 125 MHz) δ ppm:
137.35, 134.66, 134.02, 132.98, 131.66, 129.63, 129.50, 129.41, 128.98, 127.37, 126.85, 126.55, 126.25, 126.06.

Example 23

Production of 4-methoxyphenylsulfanylanisole

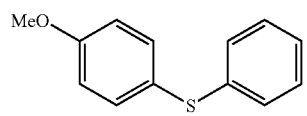

Heating and refluxing time: 15 hours.

Aryl sulfonate and its amount used:
4-Methoxyphenyl trifluoromethanesulfonate (362 μL, 2 mmol).

Thiol compound and its amount used:
Thiophenol (205 μL, 2 mmol).

Amount of Pd$_2$(dba)$_3$ used: 46 mg, 0.05 mmol.

Amount of Xantphos used: 58 mg, 0.1 mmol.

Base and its amount used:
Cs$_2$CO$_3$ (652 mg, 4 mmol).

Amount of 1,4-dioxane used: 7.2 mL.

Property, yield and yield percentage of 4-methoxyphenylsulfanylanisole:
Pale yellow liquid; yield 268 mg; yield percentage 62%.

Development solvent in flash column chromatography:
Hexane/ethyl acetate=15/1.
$^1$H NMR (500 MHz, DMSO) δ ppm:
7.41 (dt, 2H, J=6.8 Hz, 2.1 Hz), 7.13-7.24 (m, 5H), 6.89 (dt, 2H, J=6.8 Hz, 2.1 Hz), 3.81 (s, 3H).
$^{13}$C NMR (CDCl$_3$, 125 MHz) δ ppm:
160.25, 139.01, 135.76, 129.33, 128.64, 126.18, 124.75, 115.40, 55.77.

Example 24

Production of 4-nitrophenyl phenyl sulfide

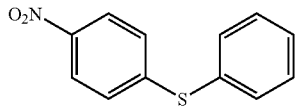

Heating and refluxing time: 13 hours.

Aryl halide and its amount used:
  4-Nitrochlorobenzene (315 mg, 2 mmol).

Thiol compound and its amount used:
  Thiophenol (205 μL, 2 mmol).

Amount of $Pd_2(dba)_3$ used: 46 mg, 0.05 mmol.

Amount of Xantphos used: 58 mg, 0.1 mmol.

Base and its amount used:
  $Cs_2CO_3$ (652 mg, 4 mmol).

Amount of 1,4-dioxane used: 6.3 mL.

Property, yield and yield percentage of 4-nitrophenyl phenyl sulfide:
  Pale yellow solid; yield 425 mg; yield percentage 92%.

Development solvent in flash column chromatography:
  Hexane/ethyl acetate=10/1.
  Melting point: 54° C.-55° C.
  $^1$H NMR ($CDCl_3$, 500 MHz) δ ppm:
  8.06 (dt, 2H, J=7.0 Hz, 2.0 Hz), 7.53-7.55 (m, 2H), 7.46 (d, 2H, J=2.4 Hz), 7.45 (d, 1H, J=1.0 Hz), 7.18 (dt, 2H, J=7.0 Hz, 2.0 Hz).
  $^{13}$C NMR ($CDCl_3$, 125 MHz) δ ppm:
  148.90, 145.78, 135.15, 130.88, 130.44, 130.07, 127.11, 124.44.

Example 25

Production of 4-nitrophenyl 2-isopropylphenyl sulfide

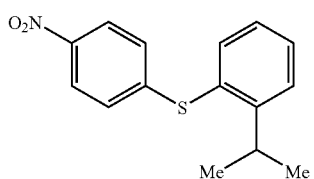

Heating and refluxing time: 8 hours.

Aryl halide and its amount used:
  4-Nitrochlorobenzene (315 mg, 2 mmol).

Thiol compound and its amount used:
  2-Isopropylbenzenethiol (303 μL, 2 mmol).

Amount of $Pd_2(dba)_3$ used: 46 mg, 0.05 mmol.

Amount of Xantphos used: 58 mg, 0.1 mmol.

Base and its amount used:
  $Cs_2CO_3$ (652 mg, 4 mmol).

Amount of 1,4-dioxane used: 6.3 mL.

Property, yield and yield percentage of 4-nitrophenyl 2-isopropylphenyl sulfide:
  Pale yellow solid; yield 410 mg; yield percentage 75%.

Development solvent in flash column chromatography:
  Hexane/ethyl acetate=5/1.
  Melting point: 91° C.-92° C.
  $^1$H NMR (500 MHz) δ ppm:
  8.03-8.06 (m, 2H), 7.50-7.54 (m, 1H), 7.46-7.49 (m, 2H), 7.25-7.28 (m, 1H), 7.05-7.08 (m, 2H), 3.47 (hept, 1H, J=6.9 Hz), 1.19 (d, 6H, J=6.9 Hz).
  $^{13}$C NMR ($CDCl_3$, 125 MHz) δ ppm:
  153.34, 149.84, 145.46, 137.32, 131.31, 128.35, 127.73, 127.44, 126.21, 124.40, 31.48, 24.15.

Example 26

Production of 2-ethylhexyl 3-phenylsulfanylpropionate

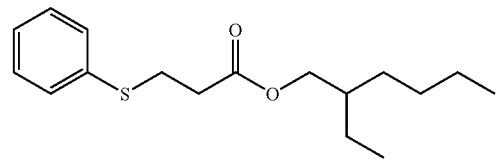

Heating and refluxing time: 6 hours.

Aryl sulfonate and its amount used:
  Benzene trifluoromethanesulfonate (324 μL, 2 mmol).

Thiol compound and its amount used:
  2-Ethylhexyl 3-mercaptopropionate (460 μL, 2 mmol).

Amount of $Pd_2(dba)_3$ used: 46 mg, 0.05 mmol.

Amount of Xantphos used: 58 mg, 0.1 mmol.

Base and its amount used:
  i-$Pr_2$NEt (700 μL, 4 mmol).

Amount of 1,4-dioxane used: 6.5 mL.

Property, yield and yield percentage of 2-ethylhexyl 3-phenylsulfanylpropionate:
  Colorless liquid; yield 530 mg; yield percentage 90%.

Development solvent in flash column chromatography:
  Hexane/ethyl acetate=10/1.
  $^1$H NMR ($CDCl_3$, 500 MHz) δ ppm:
  7.35-7.38 (m, 2H), 7.31-7.28 (m, 2H), 7.19-7.23 (m, 1H), 4.01 (dd, 2H, J=2.7 Hz, 5.7 Hz), 3.17 (dd, 2H, J=4.3 Hz, 7.4 Hz), 2.63 (dd, 2H, J=4.3 Hz, 7.4 Hz), 1.57 (m, 1H), 1.36 (m, 2H), 1.30 (m, 6H), 0.87-0.90 (m, 6H).
  $^{13}$C NMR ($CDCl_3$, 125 MHz) δ ppm:
  171.92, 135.32, 130.07, 129.02, 126.54, 67.21, 38.73, 34.49, 30.41, 29.14, 28.92, 23.79, 22.97, 14.05, 11.00.

Example 27

Production of 2-ethylhexyl 3-(4-nitrophenylsulfanyl)propionate

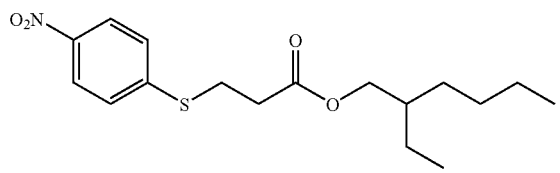

Heating and refluxing time: 13 hours.

Aryl halide and its amount used:
   4-Nitrochlorobenzene (315 mg, 2 mmol).

Thiol compound and its amount used:
   2-Ethylhexyl 3-sulfanylpropionate (460 µL, 2 mmol).

Amount of $Pd_2(dba)_3$ used: 46 mg, 0.05 mmol.

Amount of Xantphos used: 58 mg, 0.1 mmol.

Base and its amount used:
   $Cs_2CO_3$ (652 mg, 4 mmol).

Amount of 1,4-dioxane used: 6.3 mL.

Property, yield and yield percentage of 2-ethylhexyl 3-(4-nitrophenylsulfanyl)propionate:
   Colorless liquid; yield 475 mg; yield percentage 70%.

Development solvent in flash column chromatography:
   Hexane/ethyl acetate=15/1.
   $^1$H NMR (CDCl$_3$, 500 MHz) δ ppm:
   8.14 (dt, 2H, J=7.0 Hz, 2.0 Hz), 7.36 (dt, 2H, J=2.0 Hz, 7.0 Hz), 4.04 (dd, 2H, J=5.7 Hz, 3.0 Hz), 3.31 (t, 2H, J=7.3 Hz), 2.72 (t, 2H, J=7.3 Hz), 1.59 (m, 1H), 1.38-1.28 (m, 8H), 0.89 (t, 6H, J=7.3 Hz).
   $^{13}$C NMR (CDCl$_3$, 125 MHz) δ ppm:
   171.29, 146.37, 126.65, 124.10, 67.54, 38.74, 33.69, 30.40, 28.92, 27.18, 23.78, 22.97, 14.04, 10.99.

Example 28

Production of 3-(4-methoxyphenyl)sulfanylbenzenecarboxylic acid

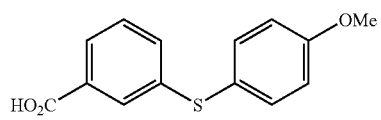

3-Bromobenzenecarboxylic acid (402 mg, 2 mmol), i-Pr$_2$NEt (700 µL, 4 mmol) and dry 1,4-dioxane (8 mL) were put into a round-bottomed flask, and the round-bottomed flask with the resulting mixture therein was purged repeated three times with nitrogen gas. Next, Pd$_2$(dba)$_3$ (46 mg, 0.05 mmol), Xantphos (58 mg, 0.1 mmol) and 4-methoxythiophenol (246 µL, 2 mmol) were added to it, and this was purged repeatedly twice with nitrogen gas, and then heated under reflux for 6 hours. Next, the completion of the reaction was confirmed through high-performance liquid chromatography, then this was cooled to room temperature, and made to have a pH of 3 to 4 with acetic acid. The insoluble matter was removed through filtration, and the filtrate was concentrated. The resulting concentrate liquid was isolated and purified through flash column chromatography (developer: hexane/ethyl acetate=10/1) with silica gel serving as a carrier, thereby giving 432 mg (yield: 83%) of 3-(4-methoxyphenyl)sulfanyl-benzenecarboxylic acid as a white solid.

Melting point: 120° C.-121° C.
   $^1$H NMR (CDCl$_3$, 500 MHz) δ ppm:
   7.89 (t, 1H, J=1.6 Hz), 7.85 (dt, 1H, J=1.6 Hz, 8.8 Hz), 7.45 (dt, 2H, J=2.1 Hz, 8.8 Hz), 7.32-7.35 (m, 2H), 6.93 (dt, 2H, J=2.1 Hz, 8.8 Hz), 3.84 (s, 3H).
   $^{13}$C NMR (CDCl$_3$, 125 MHz) δ ppm:
   171.20, 160.28, 140.16, 135.95, 132.76, 129.97, 129.15, 129.00, 127.31, 122.99, 115.27, 55.40.

Comparative Examples 1 TO 6

A compound (A) (350 mg, 2 mmol) and a compound (B) (420 mg, 3 mmol) were added to dimethoxyethane (10.5 mL), and a palladium compound (1) (10 mol %), a phosphorus compound (2) (10 mol %), and a base (3) were added to a solvent (4), and refluxed for 2 hours. The result is shown in Table 1.

Table 1 confirms the following: Even though phenyl bromide, a starting material in the invention, is used and subjected to known Suzuki-Miyaura reaction, the intended thioether compound (C) could not be obtained, or even when obtained, its yield is unsuitable for industrial production.

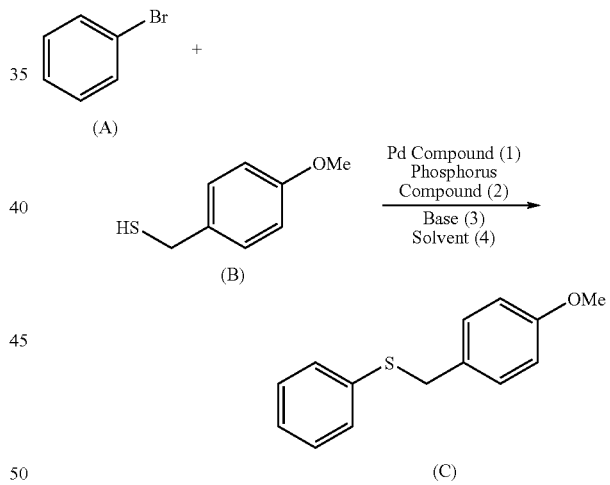

TABLE 1

| Number of Comparative Example | Pd Compound (1) | Phosphorus Compound (2) | Base (3) | Solvent (4) | Yield (%) of Compound (C) |
|---|---|---|---|---|---|
| 1 | not used | not used | KOt-Bu | DMSO | not detected |
| 2 | Pd(PPh$_3$)$_4$ | not used | KOt-Bu | dioxane | not detected |
| 3 | Pd(OAc)$_2$ | D-t-BPF | K$_2$CO$_3$ | dioxane | 10% |
| 4 | Pd(OAc)$_2$ | DPEphos | K$_2$CO$_3$ | dioxane | 21% |
| 5 | Pd(OAc)$_2$ | Xantphos | K$_2$CO$_3$ | dioxane | 32% |
| 6 | Pd(dba)$_3$ | Xantphos | K$_2$CO$_3$ | dioxane | 40% |

DMSO: dimethyl sulfoxide.
KOt-Bu: potassium t-butoxide.
D-t-BPF: 1,1'-bis(di-tert-butylphosphino)ferrocene.

DPEphos:

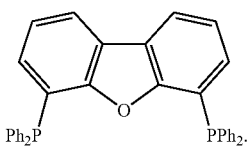

Xantphos:

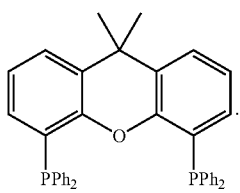

Example 29

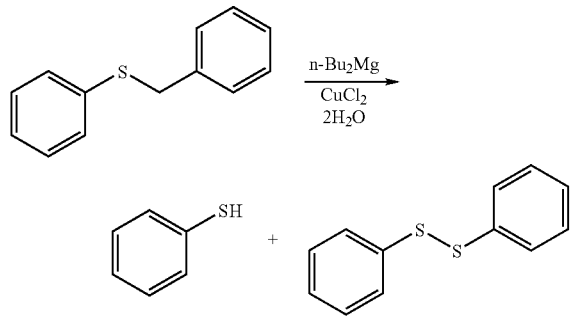

Under a nitrogen atmosphere, benzylphenyl thioether (92.5 mg, 0.462 mmol) and copper(II) chloride dihydrate (7.9 mg, 0.0463 mmol) were dissolved in diglyme (1 mL), and dibutylmagnesium 1.0 M hexane solution (1.16 mL, 1.16 mmol) was added thereto. This was heated at 50° C., stirred for 5 hours, and analyzed through high-performance liquid chromatography, which confirmed the formation of the intended thiophenol (34.6 mg; yield 68%) and diphenyl disulfide (15.1 mg; yield 30%). The recovery of the starting material, benzylphenyl thioether was 2% (1.9 mg).

Examples 30 TO 40

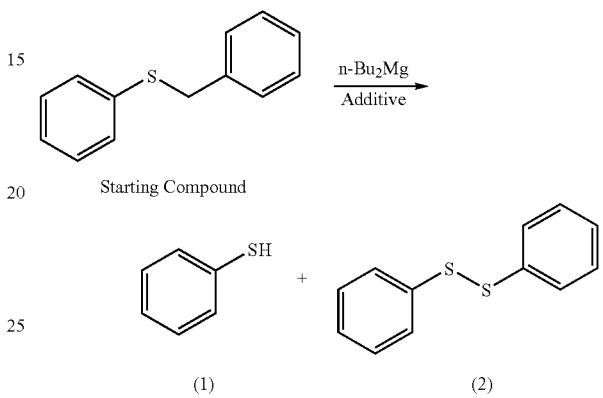

Under a nitrogen atmosphere, benzylphenyl thioether (1 equivalent) and additive (10 mmol %) were dissolved in diglyme (1 mL), and a magnesium compound, di-n-butylmagnesium 1.0 M hexane solution (2.5 equivalents) was added thereto. This was reacted under the reaction condition shown in Table 2, and the obtained reaction solution was analyzed through high-performance liquid chromatography, which confirmed the formation of the intended thiophenol (1) and diphenyl disulfide (2). The data are shown in Table 2 along with the recovery of the starting material, benzylphenyl thioether.

Table 2 confirms that the use of the additive resulted in the removal of the benzyl group.

TABLE 2

| Example No. | Additive | Reaction Temperature, °C. | Reaction Time | Recovery of Starting material | Yield of Compound (1) | Yield of Compound (2) |
| --- | --- | --- | --- | --- | --- | --- |
| 30 | CuCl$_2$•2H$_2$O | 50 | 5 | 2% | 68% | 30% |
| 31 | CuCl | 50 | 5 | 12% | 68% | 17% |
| 32 | Cu(OTf)$_2$ | 50 | 5 | 47% | 13% | 25% |
| 33 | AgNO$_3$ | 50 | 5 | 59% | 39% | 2% |
| 34 | FeCl$_2$ | 50 | 5 | 2% | 57% | 34% |
| 35 | FeCl$_3$ | 50 | 5 | 2% | 82% | 1% |
| 36 | CoCl$_2$ | 50 | 5 | 24% | 0% | 49% |
| 37 | TiCl$_2$(i-PrO)$_2$ | 50 | 5 | 28% | 68% | 1% |
| 38 | Cp$_2$TiCl$_2$ | 50 | 3 | 0% | 91% | 2% |
| 39 | Cp$_2$TiCl$_2$ | room temperature | 1 | 0% | 95% | 2% |
| 40 | Cp$_2$TiCl$_2$ | 0 | 1 | 0% | 97% | 3% |
| Comparative Example 7 | not used | 50 | 5 | 97% | 0.4% | 0% |

Tf: trifluoromethanesulfonyl group.
Cf: cyclopentadienyl group.

Example 41

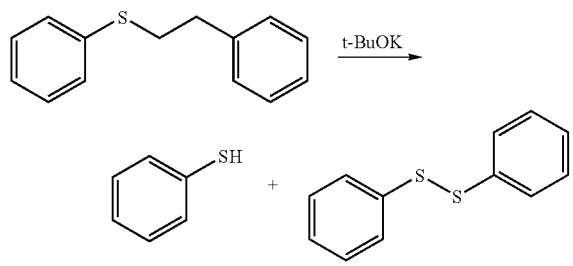

Under a nitrogen atmosphere, phenethyl phenyl thioether (99 mg, 0.462 mmol) and potassium t-butoxide (104 mg, 0.927 mmol) were suspended in N,N-dimethylacetamide (1.0 mL). This was stirred at room temperature for 2 hours, and analyzed through high-performance liquid chromatography, which confirmed the formation of the intended thiophenol (45.3 mg; yield 89%) and diphenyl disulfide (1 mg; yield 2%). The recovery of the starting material, phenethyl phenyl thioether was 0.2% (0.2 mg).

Examples 42 TO 46

Under a nitrogen atmosphere, phenethyl phenyl thioether (1 equivalent) and a base (1) were suspended in a solvent (2). This was reacted under the reaction condition shown in Table 3. The obtained reaction solution was analyzed through high-performance liquid chromatography. The yield of the intended thiophenol (a), and the recovery of the starting material, phenethyl phenyl thioether are shown below.

Table 3 confirms that, from the yield of the intended product thiophenol (a), potassium t-butoxide is industrially useful for the removal of the phenethyl group.

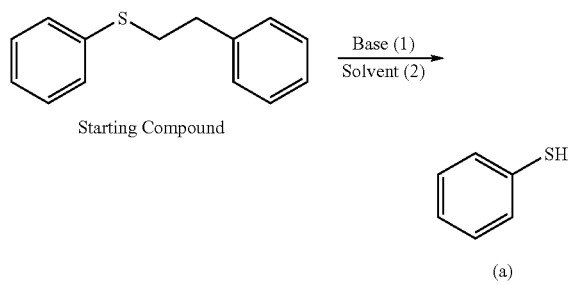

TABLE 3

| Example | Base (1) | Solvent (2) | Reaction Time | Recovery of Starting material | Yield of Compound (a) |
|---|---|---|---|---|---|
| 42 | KOt-Bu (3 eq.) | diglyme | 3 | 0% | 85% |
| 43 | KOt-Bu (3 eq.) | NMP | 3 | 0% | 90% |
| 44 | KOt-Bu (2 eq.) | NMP | 2 | 1% | 89% |
| 45 | KOt-Bu (2 eq.) | DMI | 2 | 4% | 88% |
| 46 | KOt-Bu (2 eq.) | DMSO | 2 | 0% | 93% |

TABLE 3-continued

| Example | Base (1) | Solvent (2) | Reaction Time | Recovery of Starting material | Yield of Compound (a) |
|---|---|---|---|---|---|
| Comparative Example 8 | LiOt-Bu (2 eq.) | DMA | 2 | 99% | 0% |
| Comparative Example 9 | KOH (2 eq.) | DMA | 2 | 100% | 0% |
| Comparative Example 10 | $K_2CO_3$ (2 eq.) | DMA | 2 | 100% | 0% |

DMSO: dimethylsulfoxide.
KOt-Bu: potassium t-butoxide.
LiOt-Bu: lithium t-butoxide.
DMI: 1,3-dimethyl-2-imidazolidinone.
NMP: N-methylpyrrolidone.
DMA: N,N-dimethylacetamide.

Example 47

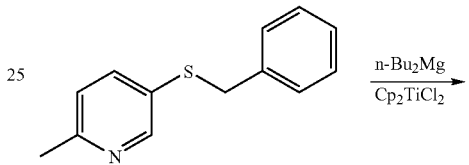

Under a nitrogen atmosphere, 2-methyl-5-benzylthiopyridine (1 equivalent) and $Cp_2TiCl_2$ (10 mmol %) were dissolved in diglyme (1 mL), and di-n-butylmagnesium (1.0 M hexane solution, 2.5 equivalents) was added thereto, and reacted at 0° C. for 1 hour. The obtained reaction solution was analyzed through high-performance liquid chromatography, which confirmed the formation of 2-methyl-5-mercaptopyridine at a yield of 100%.

The condition of the high-performance liquid chromatography employed for the analysis of the reaction solutions in Examples 29 to 47 and Comparative Examples 7 to 10 is as follows:

Column: YMC AM-303 (by YMC).

Column size:

Diameter: 4.6 mm.

Length: 250 mm.

Particle size: 5 μm.

Column temperature: 40° C.

Flow rate: 1.0 mL/min.

Detector wavelength: 220 nm.

Injection volume: 10 μL.

Mobile phase:

A: 0.1% phosphoric acid.

B: acetonitrile (MeCN).

A/B=50/50 (0 min),
  50/50 (5 min),
  10/90 (13 min),
  10/90 (20 min).

INDUSTRIAL APPLICABILITY

The production method for a thioether compound of the invention is characterized in that an easily-available bromide, chloride or sulfonate compound is used as the starting material, and this is reacted according to Suzuki-Miyaura reaction under a weak basic condition to produce the intended thioether compound at a high yield.

Accordingly, the production method of the invention has made it possible to industrially, efficiently and inexpensively produce thioether compounds for chemicals and medicines, which, however, could not be produced according to conventional Suzuki-Miyaura reaction.

In addition, according to the production method of the invention, thioether compounds can be efficiently produced from thiol compounds having a removable substituent; and according to a known method for removing a thiol-protective group or according to a method for removing a protective benzyl or phenethyl group which the present inventors have found, a thiol group may be efficiently introduced into an aryl ring or a heteroaryl ring. Therefore, the invention is useful in the field of organic synthesis.

The invention claimed is:

1. A method for producing a thioether compound or its salt of a general formula:

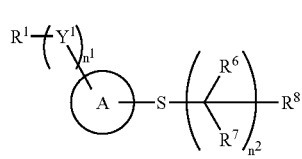

[I]

wherein $R^1$, $Y^1$, $R^6$, $R^7$, $R^8$, $n^1$, $n^2$ or a group of a general formula:

have the same meanings as mentioned below, which comprises reacting an aryl or heteroaryl compound or its salt of a general formula [III]

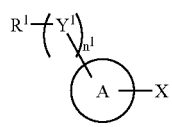

[III]

wherein $R^1$ represents a hydrogen atom, a halogen atom, a cyano group, an alkyl group having from 1 to 10 carbon atoms, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, or an alkanoyl group having from 1 to 10 carbon atoms;

$Y^1$ represents an alkylene group having from 1 to 6 carbon atoms of which the carbon chain may have a group selected from a sulfur atom, a sulfinyl group, a sulfonyl group, an oxygen atom, a carbonyl group, an oxycarbonyl group, a carbonyloxy group or a group of a general formula:

wherein $R^2$ represents a hydrogen atom, an alkyl group having from 1 to 6 carbon atoms, a benzyl group, a phenyl group, a naphthyl group or a pyridyl group;

X represents a bromine atom, a chlorine atom, a trifluoromethanesulfonyloxy group, a methylsulfonyloxy group, a benzenesulfonyloxy group, a toluenesulfonyloxy group or a nitrobenzenesulfonyloxy group;

$n^1$ indicates 0 or 1;

the group of a general formula:

means an aryl ring group or a heteroaryl ring group;

provided that when X is a chlorine atom, then the group of a general formula:

wherein $R^1$, $n^1$ and $Y^1$ have the same meanings as above] is an electron-withdrawing group, with a thiol compound or its salt of a general formula [II]:

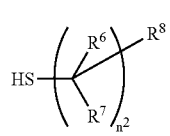

[II]

wherein $R^6$ and $R^7$ may be the same or different, each representing a hydrogen atom, an alkyl group having from 1 to 6 carbon atoms, an amino group, or a phenyl group;

$n^2$ indicates from 0 to 6;

$R^8$ represents a hydrogen atom, a halogen atom, a cyano group, an amino group, an alkyl group having from 1 to 10 carbon atoms, a trimethylsilyl group, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, an alkanoyl group having from 1 to 10 carbon atoms, or a group of a general formula:

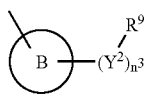

wherein $Y^2$ represents an alkylene group having from 1 to 6 carbon atoms of which the carbon chain may have a group selected from a sulfur atom, a sulfinyl group, a sulfonyl group, an oxygen atom, a carbonyl group, an oxycarbonyl group, a carbonyloxy group, and a group of a general formula:

wherein $R^7$ represents a hydrogen atom, an alkyl group having from 1 to 6 carbon atoms, a benzyl group, a phenyl group, a naphthyl group or a pyridyl group;

$n^3$ indicates 0 or 1;

$R^9$ represents a hydrogen atom, a halogen atom, a cyano group, an amino group, a nitro group, an alkyl group having from 1 to 10 carbon atoms, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, or an alkanoyl group having from 1 to 10 carbon atoms;

the group of a general formula:

means an aryl ring group or a heteroaryl ring group, in the presence of a palladium compound selected from a group consisting of palladium acetate, $Pd_2(dba)_3$ and $Pd(dba)_2$, a base selected from a group consisting of cesium carbonate, amine derivatives of a general formula:

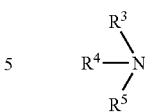

wherein $R^3$, $R^4$ and $R^5$ may be the same or different, each representing an alkyl group having from 1 to 6 carbon atoms, a benzyl group, a phenyl group or a pyridyl group, 1,5-diazabicyclo[4.3.0]non-5-ene and 1,8-diazabicyclo[5.4.0]undec-7-ene, and a phosphorus compound selected from a group consisting of a compound of a formula:

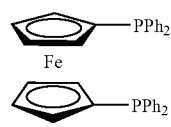

a compound of a formula:

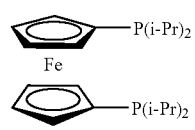

a compound of a formula:

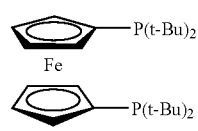

a compound of a formula:

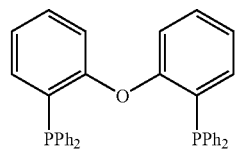

a compound of a formula:

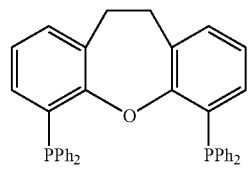

a compound of a formula:

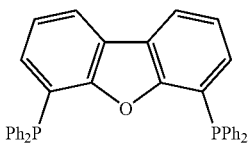

a compound of a formula:

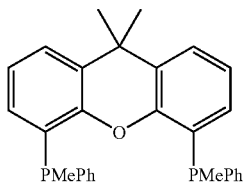

a compound of a formula:

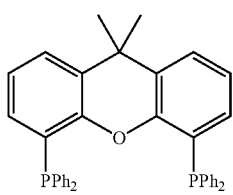

a compound of a formula:

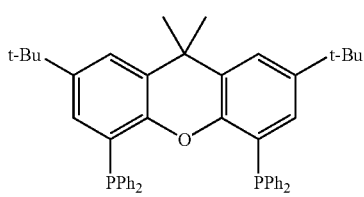

a compound of a formula:

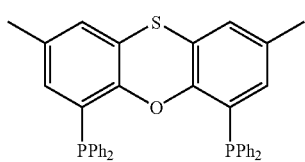

and a compound of a formula:

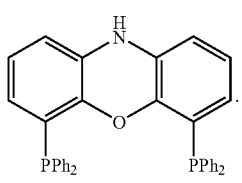

2. The method for producing a thioether compound or its salt as claimed in claim 1, wherein the thiol compound of formula [II] is a thiol compound or its salt of a general formula:

$$HS-R^e \qquad [II]$$

wherein $R^e$ represents a group of a general formula:

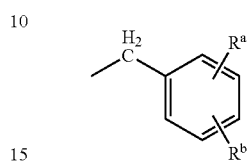

wherein $R^a$ and $R^b$ may be the same or different, each representing a hydrogen atom, an acetoxy group, a nitro group, or an alkoxy group having from 1 to 6 carbon atoms, a group of a general formula:

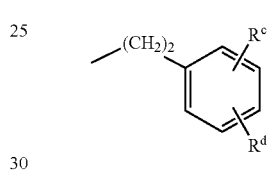

wherein $R^c$ and $R^d$ may be the same or different, each representing a hydrogen atom, a nitro group, or an alkoxy group having from 1 to 6 carbon atoms, or a group of a general formula:

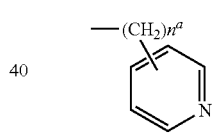

wherein $n^a$ indicates 1 or 2, or a (1-naphthyl)methyl group, a (2-naphthyl)methyl group, a 4-methoxyphenyl group, a 4-acetoxyphenyl group, a phenyl group, a trityl group, a diaminomethyl group, a 2-trimethylsilylethyl group or a ethylhexyloxycarbonyl)ethyl group.

3. The method for producing a thioether compound or its salt as claimed in claim 2, wherein $R^e$ is a group of a general formula:

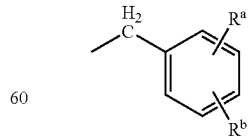

wherein $R^a$ and $R^b$ may be the same or different, each representing a hydrogen atom, an acetoxy group, a nitro group or an alkoxy group having from 1 to 6 carbon atoms, or a group of a general formula:

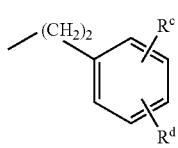

wherein $R^c$ and $R^d$ may be the same or different, each representing a hydrogen atom, a nitro group, or an alkoxy group having from 1 to 6 carbon atoms, or a group of a general formula:

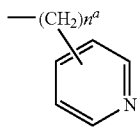

wherein $n^a$ indicates 1 or 2, or a (1-naphthyl)methyl group, or a (2-naphthyl)methyl group.

4. The method for producing a thioether compound or its salt as claimed in claim 1, wherein the thiol compound of formula [II] is a thiol compound or its salt of a general formula:

$$HS-R^f \qquad [II\text{-}b]$$

wherein $R^f$ represents a 4-pyridylethyl group, a 4-methoxyphenyl group, a 4-pyridylmethyl group, a benzyl group, a 4-acetoxybenzyl group, a 4-nitrobenzyl group, a 4-acetoxyphenyl group, a phenyl group, a trityl group, a diaminomethyl group, a 2-trimethylsilylethyl group, or a 2-(2-ethylhexyloxycarbonyl)ethyl group.

5. The method for producing a thioether compound or its salt as claimed in claim 1, wherein the palladium compound is $Pd_2(dba)_3$.

6. The method for producing a thioether compound or its salt as claimed in claim 1, wherein the phosphorus compound is a compound of a formula:

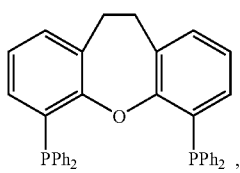

a compound of a formula:

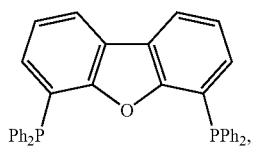

a compound of a formula:

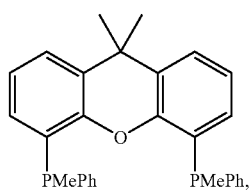

a compound of a formula:

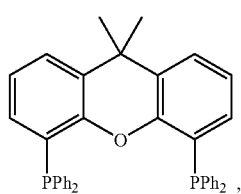

a compound of a formula:

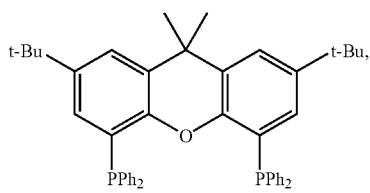

a compound of a formula:

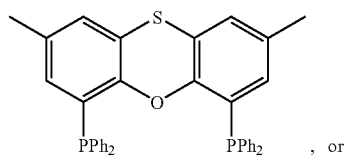

, or a compound of a formula:

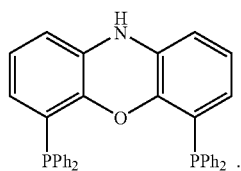

7. The method for producing as claimed in claim 1, wherein the base is cesium carbonate, diisopropylethylamine, tributylamine, triethylamine, trimethylamine, dibenzylmethylamine, 4-dimethylaminopyridine, tribenzylamine, 1,5-diazabicyclo[4.3.0]non-5-ene, or 1,8-diazabicyclo[5.4.0]undec-7-ene.

8. The method for producing a thioether compound or its salt as claimed in claim 1, wherein the base is diisopropylethylamine.

9. The method for producing a thioether compound or its salt as claimed in claim 1, wherein the palladium compound is Pd$_2$(dba)$_3$, the phosphorus compound is a compound of a formula:

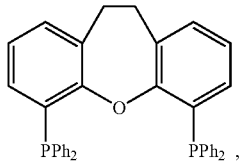

a compound of a formula:

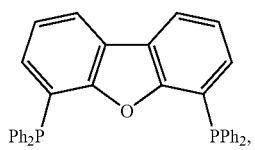

a compound of a formula:

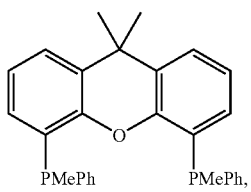

a compound of a formula:

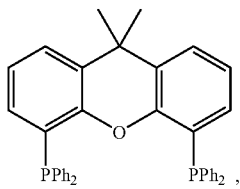

a compound of a formula:

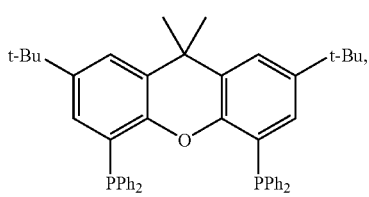

a compound of a formula:

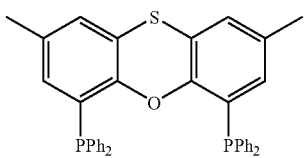

or a compound of a formula:

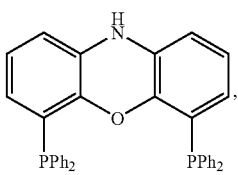

and the base is cesium carbonate, diisopropylethylamine, tributylamine, triethylamine, dibenzylmethylamine, 1,5-diazabicyclo[4.3.0]non-5-ene, or 1,8-diazabicyclo[5.4.0]undec-7-ene.

10. A method for producing a thiol compound or its salt of a general formula [I-b]:

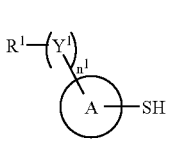    [I-b]

wherein R$^1$, Y$^1$, n$^1$ or the group of a general formula:

have the same meanings as mentioned below], which comprises reacting an aryl or heteroaryl compound or its salt of a general formula [III]:

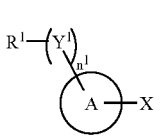    [III]

wherein R$^1$ represents a hydrogen atom, a halogen atom, a cyano group, an alkyl group having from 1 to 10 carbon atoms, an alkoxy group having from 1 to 10 carbon atoms, an alkylthio group having from 1 to 10 carbon atoms, an alkylsulfinyl group having from 1 to 10 carbon atoms, an alkylsulfonyl group having from 1 to 10 carbon atoms, a hydroxyl group, a carboxyl group, an alkoxycarbonyl group having from 2 to 10 carbon atoms, an alkanoyloxy group having from 2 to 10 carbon atoms, an aryl group, an arylcarbonyl group, an arylcarbonyloxy group, a heteroaryl group, a heteroarylcarbonyl group, a heteroarylcarbonyloxy group, a nitro group, an alkanoylamino group having from 1 to 10 carbon atoms, an arylcarbonylamino group, a heteroarylcarbonylamino group, or an alkanoyl group having from 1 to 10 carbon atoms;

$Y^1$ represents an alkylene group having from 1 to 6 carbon atoms of which the carbon chain may have a group selected from a sulfur atom, a sulfinyl group, a sulfonyl group, an oxygen atom, a carbonyl group, an oxycarbonyl group, a carbonyloxy group and a group of a general formula:

wherein $R^2$ represents a hydrogen atom, an alkyl group having from 1 to 6 carbon atoms, a benzyl group, a phenyl group, a naphthyl group or a pyridyl group;

X represents a bromine atom, a chlorine atom, a trifluoromethanesulfonyloxy group, a methylsulfonyloxy group, a benzenesulfonyloxy group, a toluenesulfonyloxy group or a nitrobenzenesulfonyloxy group;

$n^1$ indicates 0 or 1;

the group of a general formula:

means an aryl ring group or a heteroaryl ring group;

provided that when X is a chlorine atom, then the group of a general formula:

is an electron-attracting group, wherein $R^1$, $n^1$ and $Y^1$ have the same meanings as above, with a thiol compound or its salt of a general formula [II-a]:

         [II-a]

wherein $R^e$ represents a group of a general formula:

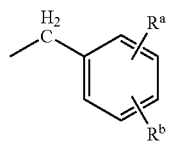

wherein $R^a$ and $R^b$ may be the same or different, each representing a hydrogen atom, an acetoxy group, a nitro group, or an alkoxy group having from 1 to 6 carbon atoms, a group of a general formula:

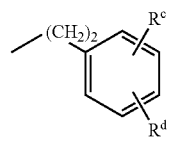

wherein $R^c$ and $R^d$ may be the same or different, each representing a hydrogen atom, a nitro group, or an alkoxy group having from 1 to 6 carbon atoms, or a group of a general formula:

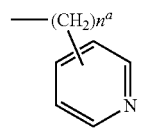

wherein $n^a$ indicates 1 or 2, or a (1-naphthyl)methyl group, a (2-naphthyl)methyl group, a 4-methoxyphenyl group, a 4-acetoxyphenyl group, a phenyl group, a trityl group, a diaminomethyl group, a 2-trimethylsilylethyl group or a 2-(2-ethylhexyloxycarbonyl)ethyl group, in the presence of a palladium compound selected from a group consisting of palladium acetate, $Pd_2(dba)_3$ and $Pd(dba)_2$, a base selected from a group of consisting of cesium carbonate, amine derivatives of a general formula:

wherein $R^3$, $R^4$ and $R^5$ may be the same or different, each representing an alkyl group having from 1 to 6 carbon atoms, a benzyl group, a phenyl group or a pyridyl group, 1,5-diazabicyclo[4.3.0]non-5-ene and 1,8-diazabicyclo[5.4.0]undec-7-ene, and a phosphorus compound selected from a group consisting of a compound of a formula:

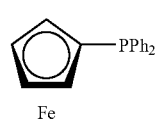
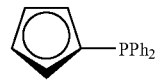

a compound of a formula:

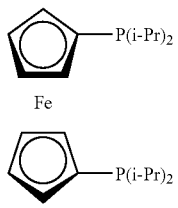

a compound of a formula:

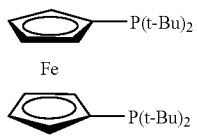

a compound of a formula:

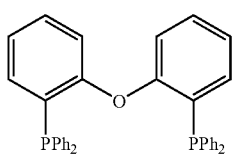

a compound of a formula:

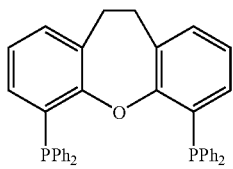

a compound of a formula:

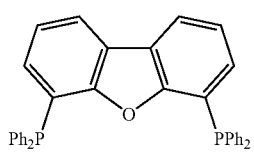

a compound of a formula:

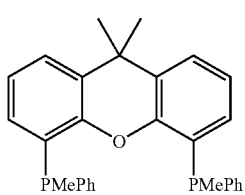

a compound of a formula:

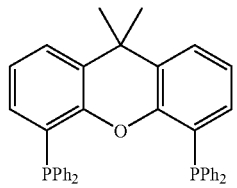

a compound of a formula:

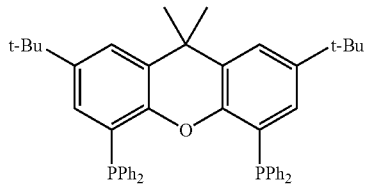

a compound of a formula:

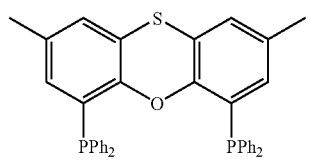

and a compound of a formula:

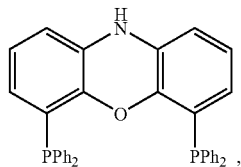

thereby affording a thioether compound or its salt of a general formula [I-a]:

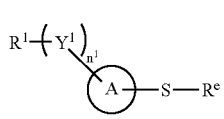

wherein $R^1$, $Y^1$, $R^e$, $n^1$ and the group of a general formula:

have the same meanings as above],
and then removing the protective group of $R^e$ of the resulting thioether compound of formula [I-a].

11. The method for producing as claimed in claim 1, wherein the alkylene group having from 1 to 6 carbon atoms, of which the carbon chain may have a group of a general formula:

wherein $R^7$ represents a hydrogen atom, an alkyl group having from 1 to 6 carbon atoms, a benzyl group, a phenyl group, a naphthyl group or a pyridyl group, is a methylene group, an ethylene group, a trimethylene group, a tetramethylene group, a pentamethylene group, a hexamethylene group, a propylene group, an ethylethylene group, or a group of a general formula:

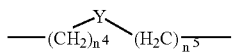

wherein Y represents a sulfur atom, a sulfinyl group, a sulfonyl group, an oxygen atom, a carbonyl group, an oxycarbonyl group, a carbonyloxy group, and a group of a general formula:

wherein $R^2$ represents a hydrogen atom, an alkyl group having from 1 to 6 carbon atoms, a benzyl group, a phenyl group, a naphthyl group or a pyridyl group; $n^4$ and $n^5$ each indicate an integer of from 1 to 6, and the sum of the two must not be more than 6.

12. The method for producing as claimed in claim 1, wherein $n^1$ is 0.

13. The method for producing as claimed in claim 1, wherein $n^2$ is 0.

14. The method for producing as claimed in claim 1, wherein $n^3$ is 0.

15. The method for producing a thiol compound or its salt as claimed in claim 10, wherein the base is cesium carbonate, diisopropylethylamine, tributylamine, triethylamine, trimethylamine, dibenzylmethylamine, 4-dimethylaminopyridine, tribenzylamine, 1,5-diazabicyclo[4.3.0]non-5-ene, or 1,8-diazabicyclo[5.4.0]undec-7-ene.

16. The method for producing a thiol compound or its salt as claimed in claim 10, wherein the palladium compound is $Pd_2(dba)_3$, the phosphorus compound is a compound of a formula:

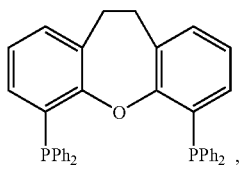

a compound of a formula:

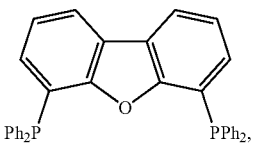

a compound of a formula:

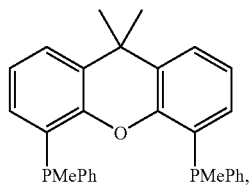

a compound of a formula:

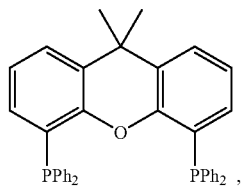

a compound of a formula:

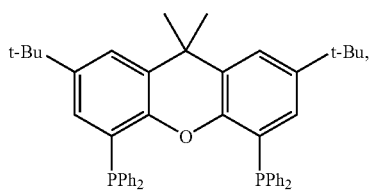

a compound of a formula:

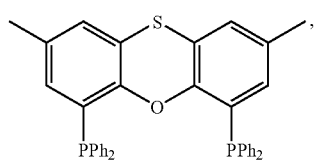

or a compound of a formula:

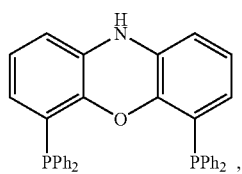

and the base is cesium carbonate, diisopropylethylamine, tributylamine, triethylamine, trimethylamine, dibenzylmethylamine, 4-dimethylaminopyridine, tribenzylamine, 1,5-diazabicyclo[4.3.0]non-5-ene, or 1,8-diazabicyclo[5.4.0]undec-7-ene.

17. The method for producing a thiol compound or its salt as claimed in claim 10, wherein the protective group of $R^e$ is a group of a general formula:

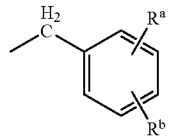

wherein $R^a$ and $R^b$ may be the same or different, each representing a hydrogen atom, an acetoxy group, a nitro group, or an alkoxy group having from 1 to 6 carbon atoms, a group of a general formula:

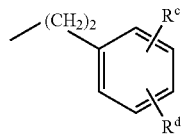

wherein $R^c$ and $R^d$ may be the same or different, each representing a hydrogen atom, a nitro group, or an alkoxy group having from 1 to 6 carbon atoms,
a (1-naphthyl)methyl group, or a (2-naphthyl)methyl group.

18. The method for producing a thiol compound or its salt as claimed in claim 10, wherein the protective group of $R^e$ is a group of a general formula:

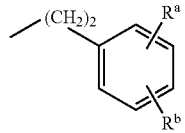

wherein $R^c$ and $R^d$ may be the same or different, each representing a hydrogen atom, a nitro group, or an alkoxy group,
and the step of removing the protective group of $R^e$ comprises treatment with a potassium alkoxide or a sodium alkoxide.

19. The method for producing a thiol compound or its salt as claimed in claim 10, wherein the protective group of $R^e$ is a group of a general formula:

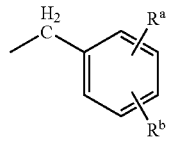

wherein $R^a$ and $R^b$ may be the same or different, each representing a hydrogen atom, an acetoxy group, a nitro group, or an alkoxy group having from 1 to 6 carbon atoms,
a (1-naphthyl)methyl group or a (2-naphthyl)methyl group, and the step of removing the protective group of $R^e$ comprises treatment with a magnesium compound of a general formula:

wherein $R^g$ represents a halogen atom, or an alkyl group having from 1 to 10 carbon atoms; $R^h$ represents an alkyl group having from 1 to 10 carbon atoms,
in the presence of one additive selected from a group consisting of copper compounds, iron compounds, cobalt compounds, silver compounds, titanium compounds or their hydrates.

20. The method for producing a thiol compound or its salt as claimed in claim 19, wherein the additive is $CuCl_2$, $CuCl_2.2H_2O$, $FeCl_3$, $FeCl_2$, $TiCl_2(i-PrO)_2$, $Cu(CF_3SO_2O)_2$, $CoCl_2$, $AgNO_3$ or $Cp_2TiCl_2$.

21. The method for producing a thiol compound or its salt as claimed in claim 19, wherein the magnesium compound is dimethylmagnesium, diethylmagnesium, di-n-butylmagnesium, di-n-propylmagnesium, n-butylmagnesium chloride, n-butylmagnesium bromide, methylmagnesium chloride, methylmagnesium bromide, ethylmagnesium chloride, ethylmagnesium bromide, n-propylmagnesium chloride, n-propylmagnesium bromide, isopropylmagnesium chloride or isopropylmagnesium bromide.

22. The method for producing as claimed in claim 10, wherein the alkylene group having from 1 to 6 carbon atoms, of which the carbon chain may have a group of a general formula:

wherein $R^7$ represents a hydrogen atom, an alkyl group having from 1 to 6 carbon atoms, a benzyl group, a phenyl group, a naphthyl group or a pyridyl group], is a methylene group, an ethylene group, a trimethylene group, a tetramethylene group, a pentamethylene group, a hexamethylene group, a propylene group, an ethylethylene group, or a group of a general formula:

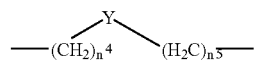

wherein Y represents a sulfur atom, a sulfinyl group, a sulfonyl group, an oxygen atom, a carbonyl group, an oxycarbonyl group, a carbonyloxy group, and a group of a general formula:

wherein $R^2$ represents a hydrogen atom, an alkyl group having from 1 to 6 carbon atoms, a benzyl group, a phenyl group, a naphthyl group or a pyridyl group; $n^4$ and $n^5$ each indicate an integer of from 1 to 6, and the sum of the two must not be more than 6.

23. The method for producing as claimed in claim 10 wherein $n^1$ is 0.

24. The method for producing as claimed in claim 10 wherein $n^2$ is 0.

25. The method for producing as claimed in claim 10 wherein $n^3$ is 0.

* * * * *